United States Patent [19]

Logue

[11] Patent Number: 5,532,591
[45] Date of Patent: Jul. 2, 1996

[54] APPARATUS FOR DETECTING SURFACE FLAWS IN CYLINDRICAL ARTICLES BY MEANS OF ASYMMETRIC MAGNETIC DETECTION

[76] Inventor: Delmar L. Logue, R.R. #1, Box 60, Herrick, Ill. 62431

[21] Appl. No.: 142,933

[22] Filed: Oct. 29, 1993

Related U.S. Application Data

[63] Continuation-in-part of Ser. No. 108,880, Aug. 13, 1993, abandoned, and a continuation-in-part of Ser. No. 842,244, Feb. 27, 1992, Pat. No. 5,404,101.
[51] Int. Cl.⁶ .......................... G01N 27/82; G01N 27/90; G01R 33/12; B07C 5/344
[52] U.S. Cl. .......................... 324/242; 209/567; 324/232; 324/233
[58] Field of Search .................... 324/219–221, 324/226, 227, 232, 233, 239–243, 262; 209/562, 567

[56] References Cited

U.S. PATENT DOCUMENTS

| | | | |
|---|---|---|---|
| 4,002,966 | 1/1977 | Hinds et al. | 324/232 |
| 4,785,243 | 11/1988 | Abramczyk et al. | 324/242 X |
| 5,119,023 | 6/1992 | Lloyd | 324/239 |
| 5,130,653 | 7/1992 | Wu et al. | 324/241 |
| 5,311,127 | 5/1994 | Bisiaux | 324/242 X |

*Primary Examiner*—Gerard R. Strecker

[57] ABSTRACT

An apparatus for detecting surface flaws in cylindrical articles by means of asymmetric magnetic detection, utilizing a rotating magnetic field, said articles having central longitudinal axes, apparatus having a guide assembly for guiding the cylindrical articles along a displacement path having a central longitudinal axis extending coaxially of the central longitudinal axes of the articles and a pair of multiple polar sensor assemblies positioned in annular relationship with the displacement path for producing a plurality of phase/amplitude modulated signals representative of the surface geometry of the inspected cylindrical article, also disclosed are two embodiments of cylindrical container flange imperfection detector apparatus utilizing multiple polar sensor assemblies.

18 Claims, 18 Drawing Sheets

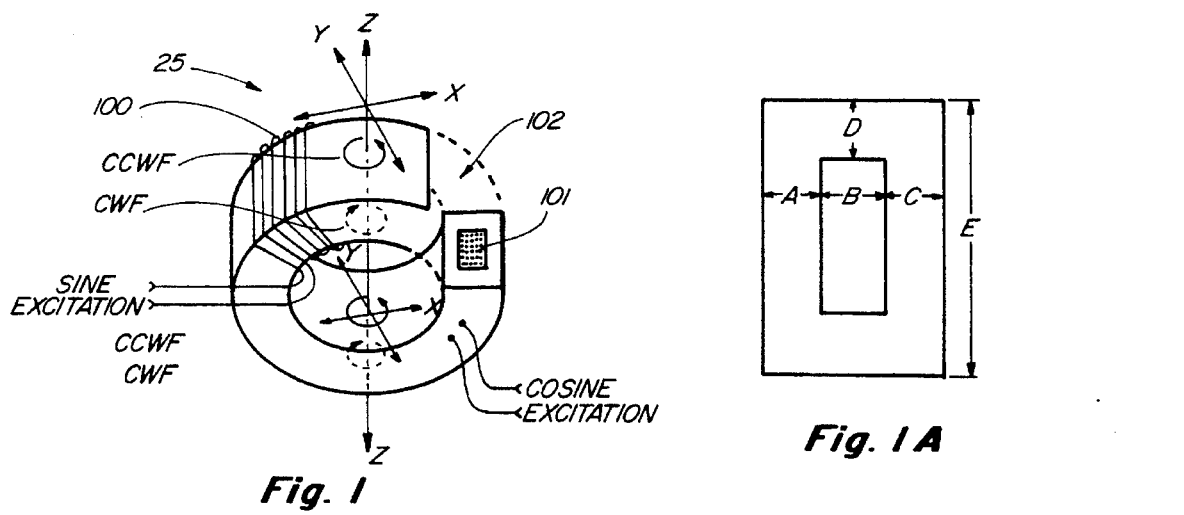
Fig. 1
Fig. 1A
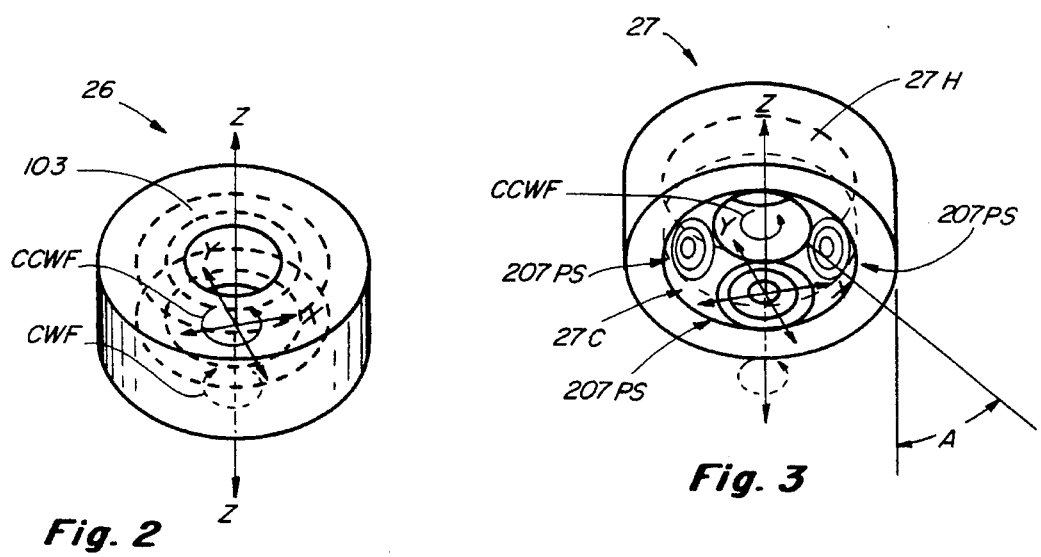
Fig. 2
Fig. 3
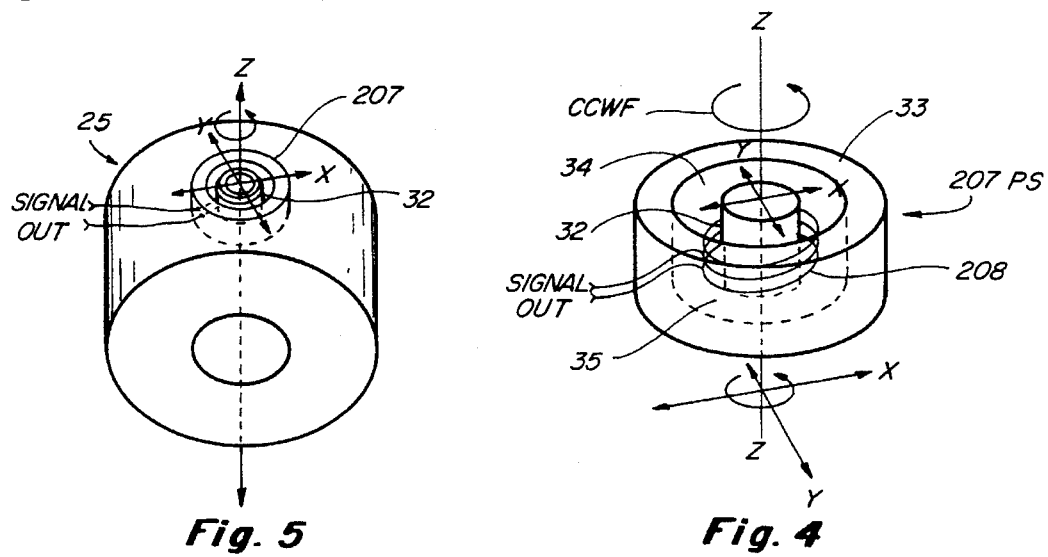
Fig. 5
Fig. 4

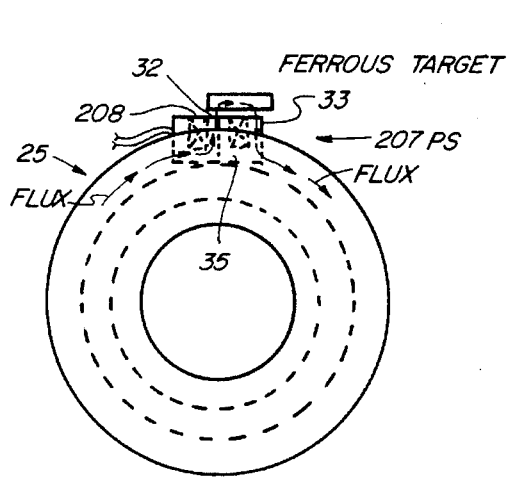
Fig. 6
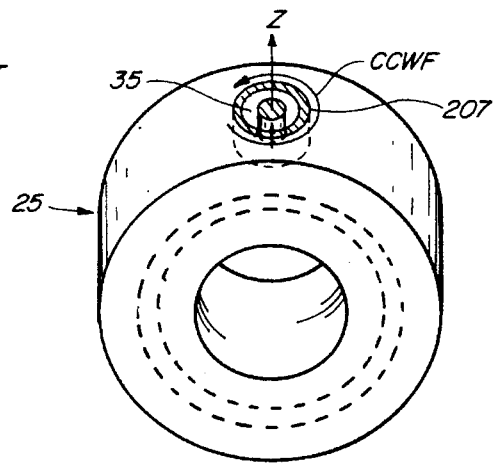
Fig. 7
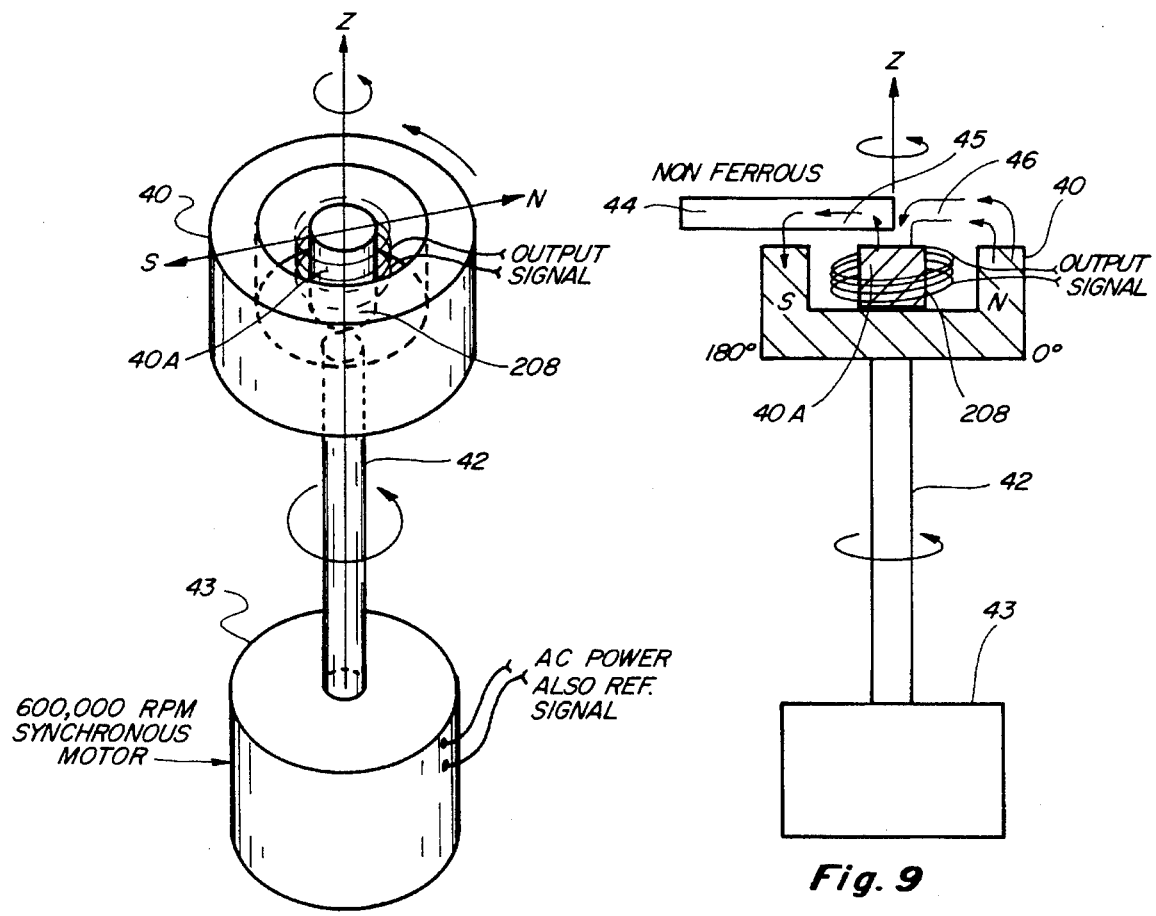
Fig. 8
Fig. 9

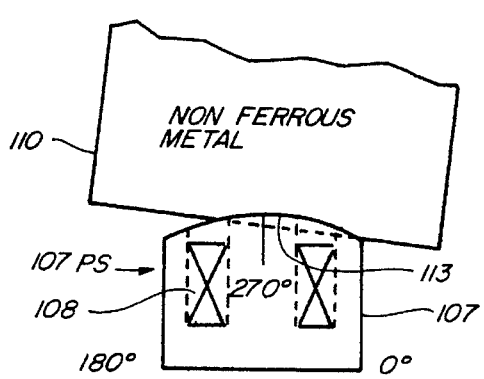
Fig. 17
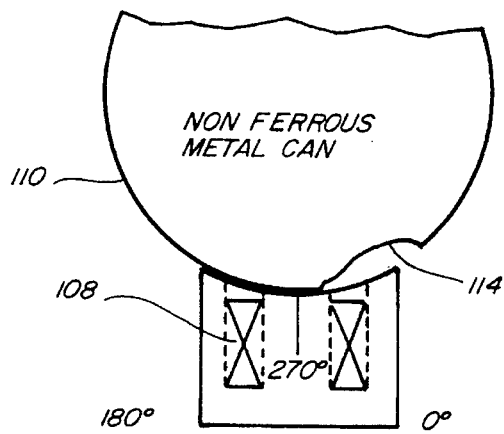
Fig. 18
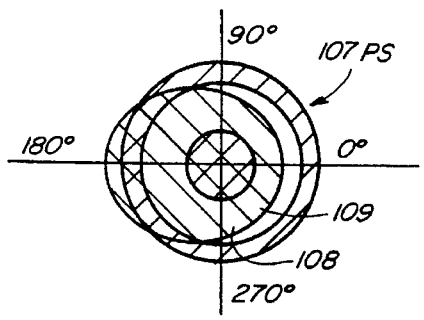
Fig. 17A
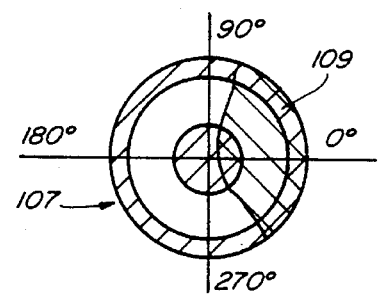
Fig. 18A
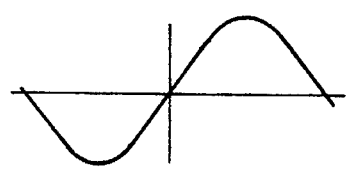
Fig. 17B
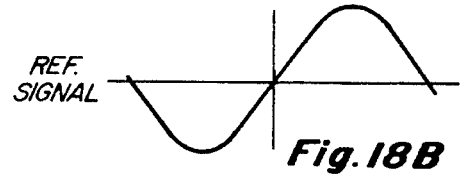
Fig. 18B
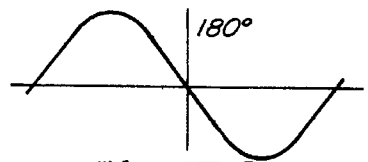
Fig. 17C
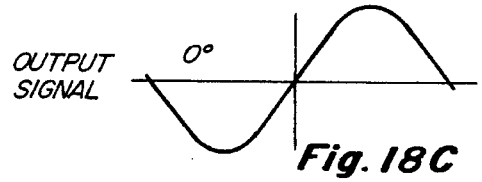
Fig. 18C
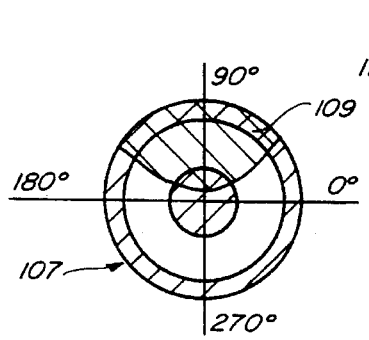
Fig. 19A
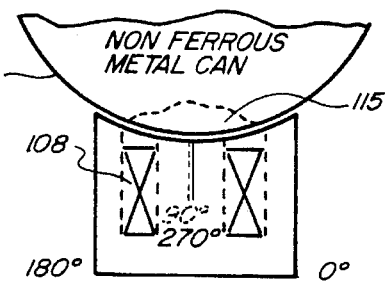
Fig. 19
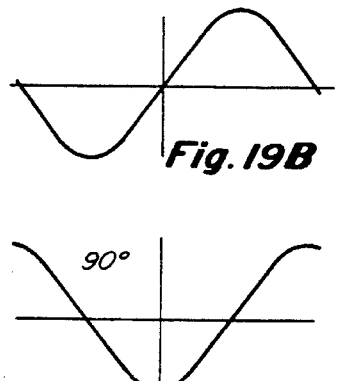
Fig. 19B
Fig. 19C

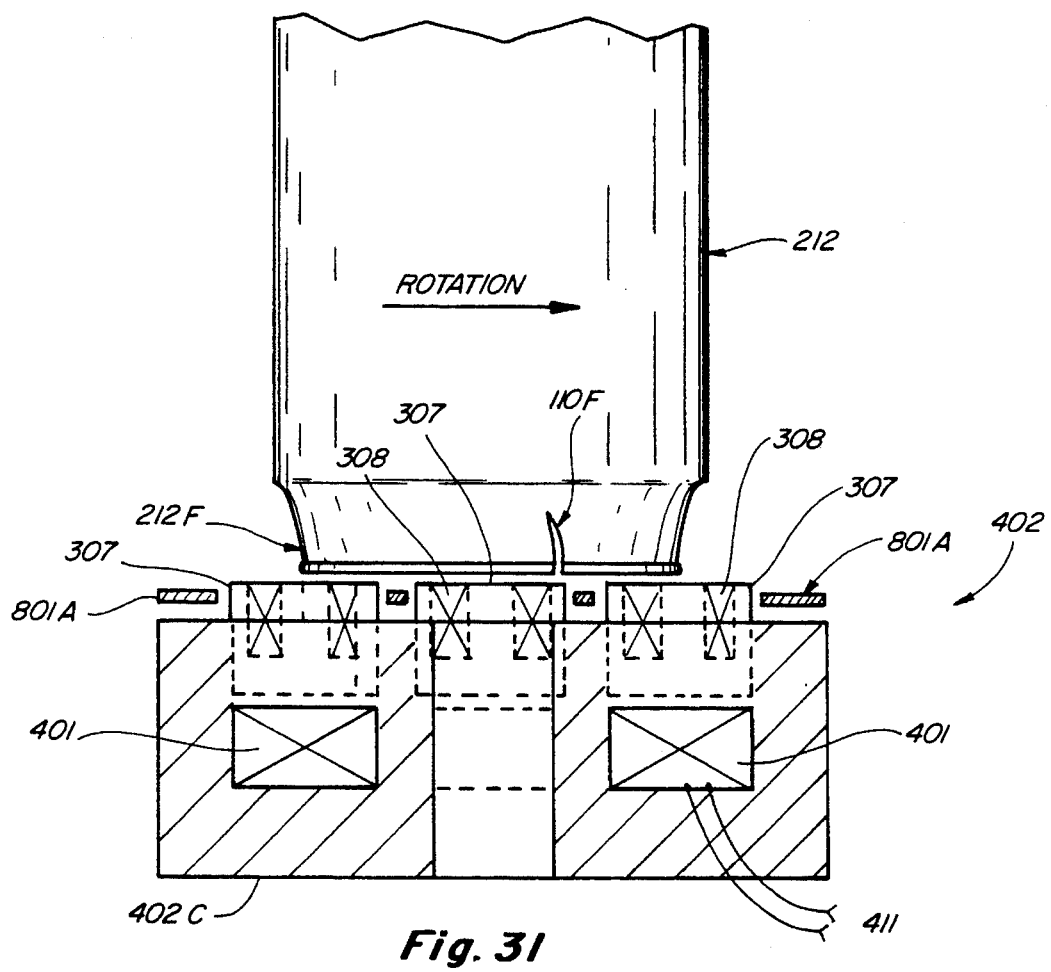
Fig. 31
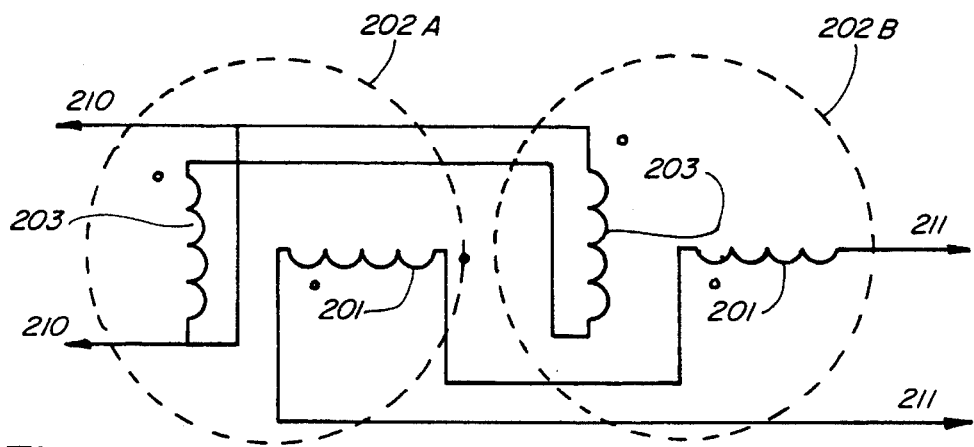
Fig. 34
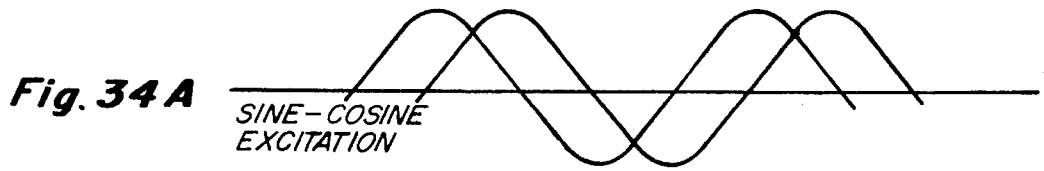
Fig. 34A  SINE-COSINE EXCITATION

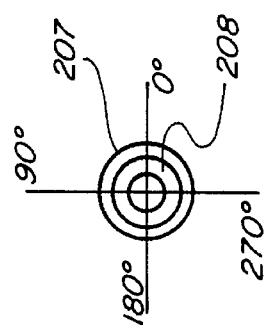
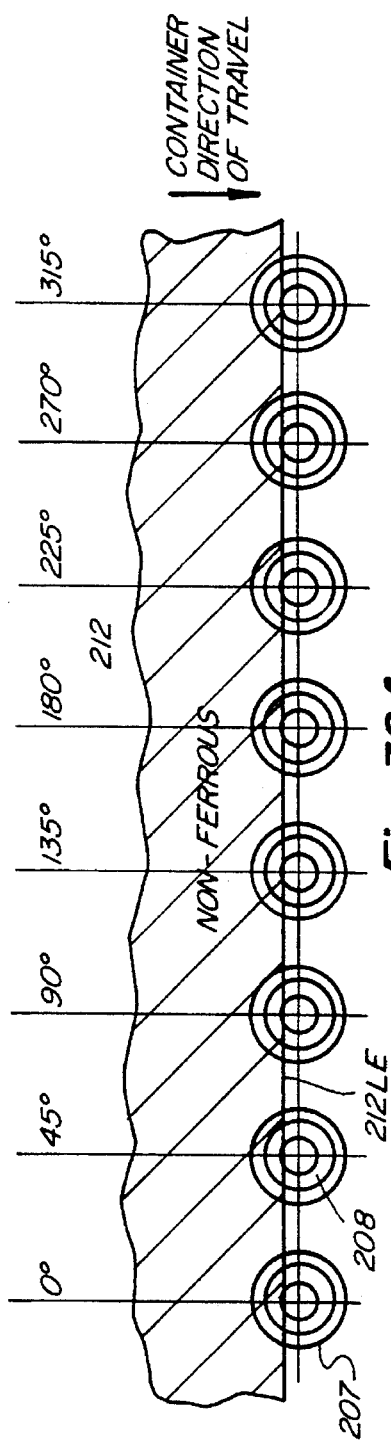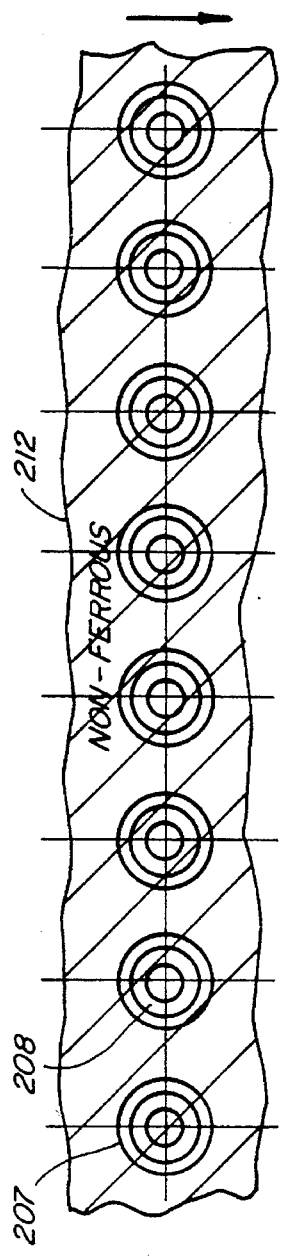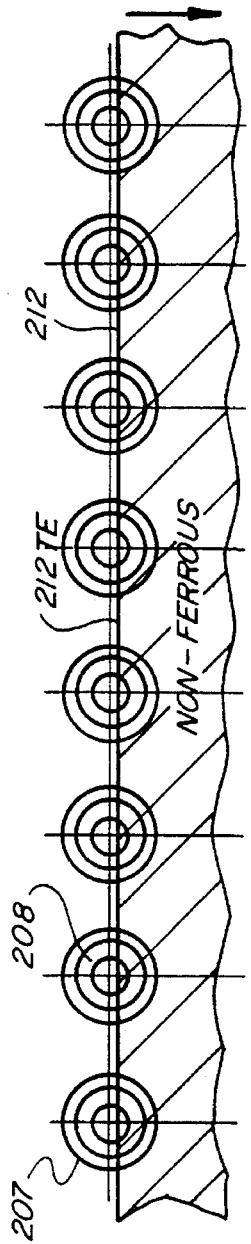

APPARATUS FOR DETECTING SURFACE FLAWS IN CYLINDRICAL ARTICLES BY MEANS OF ASYMMETRIC MAGNETIC DETECTION

This application is a continuation in part of U.S. patent application Ser. No. 07/842,244 filed on Feb. 27, 1992, now U.S. Pat. No. 5,404,101, entitled Rotary Sensing Device, and also patent application Ser. No. 08/108,880 filed Aug. 13, 1993, now abandoned, entitled Rotating Magnetic Field Devices, both by the same applicant.

INCORPORATION BY REFERENCE

U.S. Pat. No. 5,130,653 to Wu et al., U.S. Pat. No. 4,029,958 to Wright, and U.S. Pat. No. 4,002,966 to Hinds et al. are incorporated by reference herein as illustrating the art to which the present invention is particularly directed and describing the mechanical aspects of the apparatus in which the disclosed sensors can be used.

BACKGROUND

The present invention relates to the detection of surface flaws in manufactured articles and more particularly, to the detection of surface flaws in manufactured articles such as can bodies. Even though prior art has provided a number of inductive sensors, such as reluctance, eddy:current, Hall effect, and bridge type using a pair of inductors, the known art is still dependent on the impedance variation of an AC excited uniaxial inductor in proximity to either a ferrous or non-ferrous target. Many types of conventional inductive sensors have been adapted to the detection of dents in the sidewall of a container, such as the Wu et al. U.S. Pat. No. 5,130,653 which utilizes two spool type eddy current sensors connected in a differential bridge circuit. These two spools are coaxially mounted in an axial guide path for the inspected cans. Although this was a step in the right direction for higher line speeds, the spool type sensors have an unfavorable signal/noise ratio because:

$$\text{flaw signal} = \frac{\text{total sensor pick-up area}}{\text{flaw area}}$$

In the Wu et al. patent at any given inspection interval each spool type detector coil is receiving an eddy current signal representing a band-like portion encircling the circumference of the can, of which a modest dent (⅛") makes up only a small portion of the total eddy current value being scanned at any given instant. To extract the desired dent signal from this band-like eddy current signal, of course a very high gain pre-amplifier and filter is required, with it's attendant thermal drift, and meticulous balancing procedure. The very careful tweaking adjustments are disclosed in col. 12, line 1, and col. 11, line 1, of the cited patent. The detection system of the present invention utilizes two groups of eight, each circularly arranged rotating magnetic field sensors, to scan the sidewalls of the inspected containers at sixteen longitudinal positions around the cans as they traverse the axial path. In the present sensing apparatus the total sensor area/flaw area ratio is more favorable being divided.

The present sensor is inherently-self balanced, which completely eliminates manual tweaking adjustments.

Also in container manufacture the flange portion of the container must be inspected for cracks and dents before the end is sealed in place. The Wright U.S. Pat. No. 4,029,958 discloses a flange flaw detection apparatus in which the container flange is rapidly rotated near a permanent magnet coupling flux to a pick-up coil.

Dents or cracks in the rotating flange thus produce a changing field coupled to the pick-up coil, generating a flaw signal, the resultant amplitude thus depending on the rotational speed of the container. The sensing frequency is directly related to the rpm of the can (less than 50 hz). Since frequency is a factor of induction, this method is not as sensitive as an oscillator driven unit, and the mechanical rotating equipment is a disadvantage. The Hinds et al. U.S. Pat. No. 4,002,966 discloses another apparatus for detecting flaws in the flange of a container, in which the container flange is rotated near an ac driven field proximity sensor, and the induced eddy current signal is compared to a reference value to extract the flaw signal.

SUMMARY OF THE INVENTION

An object of the present invention is to provide a flaw detection apparatus utilizing multiple polar sensors mounted in bores in the inside diameter wall of two hollow toroid cores, providing multiple overlapping surface geometry sensing of a cylindrical container sidewall.

An object of the instant invention is to provide a cylindrical article flaw detection apparatus utilizing multiple asymmetric detection.

One objective of the present invention is to provide a flaw sensing apparatus that is inherently self balanced, due to the symmetrical geometry of the polar sensor face, and the circularly polarized rotating field, so that amplifier offset balancing is eliminated.

Another object of the present invention-is to provide a sensor inherently immune to external electromagnetic interference: (1) an inherent constant flux level existing throughout the entire hollow toroid core; (2) the mounted polar sensors being surrounded by this constant level of magnetic flux.

(3) two inherently closed magnetic circuits existing within a hollow toroid core (sine-cosine excitation).

A further object of the present invention is to provide a multiple polar sensor apparatus in which each polar sensor has a 360 degree symmetrical flux pattern, for detecting surface asymmetrics in cylindrical articles, by means of symmetric/asymmetric comparison.

Another object of the present invention is to provide a sensing apparatus in which the sensors that detect container sidewall dents also indicate the presence or absence of the inspected container in each of the two inspection zones. By utilizing integral combinations of the signals from each of the two multiple polar sensor assemblies, the leading and trailing edges of the inspected can may be known, thus eliminating the need for auxiliary light beam sensors.

It is also an object of the present invention to provide a sensor apparatus that is of simple construction, utilizing pot core technology.

It is also an object of the present invention to provide a can inspection apparatus that accommodates a continuous stream of touching cans, thus eliminating the time delay of waiting for a can to fall through the two inspection zones.

Rotating magnetic field sensor fundamentals

In view of the fact that rotating magnetic fields have had very limited application to inductive sensing in prior art, the applicant believes it proper to describe the fundamentals of the present invention. Referring now to FIG. 1, a hollow toroid core 25 is shown in cross-sectional view. The inside winding excitation winding 101, has connecting leads labeled COSINE EXCITATION.

It is believed by the inventor that the cross section dimensions of the hollow toroid core should be according to the approximate dimensions shown in FIG. 1A where dimensions A, B, C, and D are shown approximately equal. This is believed to be the best proportions between the two orthogonal flux circuits shown in FIG. 1. The dimension E may be varied to suit the application. FIG. 1 shows the outside winding 100 wound around a portion of the core 25 having connecting leads SINE EXCITATION. When sine-cosine excitation is applied to the inside and outside windings a rotating magnetic field is created throughout the entire core. The axis of each rotating domain being perpendicular to the surface of the core everywhere. This hollow toroid inductor is the one geometric shape in which the entirety of the core inherently has:

(1) orthogonality between two magnetic circuits.

(2) two completely closed magnetic circuits.

(3) a sine-cosine generated rotating magnetic field.

(4) a constant flux density.

(5) multiple sensor capability.

Refer now to FIG. 1 to determine the field rotational relationships at four points of a z-axis diametrical line intersecting the hollow toroid wall at four places.

The solid and dashed circular arrows CCWF, and CWF indicate counter-clockwise and clockwise rotational directions.

In FIG. 2 a hollow toroid core 26 is lying on its side. The Z-axis line intersects the side walls of the core 26 at two points. The solid and dashed circular arrows indicate the relative field rotational directions. The hollow area is 103 (inside and outside windings have been omitted for clarity). FIG. 3 is a perspective view of a hollow toroid 27 having a conical inside diameter 270 with four polar sensors 207PS mounted in bores in the conical portion 27C. The Z-axis line indicates that the axis of the polar sensors 207PS are at an angle A to the axis of the hollow core 27. The hollow inside is indicated by 27H. The cores in FIGS. 1, 2, 3, 4, and 5 are all made of ferromagnetic material.

FIG. 4 is an enlarged view of a polar sensor 207PS detailing its structure. The central pole 32 is surrounded by the concentric outer pole 33, providing an annular coil space 34, the two poles being connected by means or a base portion 35, this complete core being the same as a conventional pot core half. The signal coil 208 is wound around the central pole 32, and has connecting leads SIGNAL OUT. Polar sensor 207PS has polar coordinate proximity sensing characteristics being:

(a) 360 degree directional indicating by phase modulation.

(b) distance indicating by amplitude modulation.

(c) signal nulled when no target is present.

(d) signal nulled when the flux is symmetrically balanced.

These unique features will become apparent later in the detailed description section.

FIG. 4 shows how the pick-up core 207 (the polar sensor proper is made up of a pick-up core 207, and a pick-up coil 208 wound around central pole 32). This polar sensor is mounted partially within a bore disposed in the wall of a hollow toroid core 25 as in FIGS. 6 and 7.

With the Z-axis of the pick-up core 207 perpendicular to the surface of hollow toroid core 25, the rotating field is coupled all around the pick-up core 207. Please notice that the pick-up coil 208 is positioned coplaner to the rotating field, thus with no target present no flux coupling occurs and no signal is produced. FIG. 6 is a side view of hollow core 25, and also an axial view of pick-up core 207 and pick-up coil 208. A target labeled FERROUS TARGET is shown coupling flux from the hollow toroid core, through the base portion 35, up through the central pole 32, through the ferrous target, and down through the concentric outer pole 33 back again to the hollow toroid core. Thus a portion of the flux rotating in hollow toroid 25 is linking the pick-up coil 208, producing a signal.

FIG. 7 is a perspective view of hollow toroid core 25, showing the mounted pick-up core 207 having the annular coil space 35 (the coil is not shown). The circular arrow CCWF indicates the rotating field, the axis of rotation is Z. The inside and outside windings of core 25 are not shown in FIG. 7 for clarity.

Due to the fact that the concept of a constant (non-collapsing) magnetic flux level is not associated with conventional signal transformers, I will use a spinning permanent magnet to illustrate the rotating magnetic field at the face of the polar sensor 207PS. Referring now to FIG. 8, a permanent magnet in the shape of a pot core half 40 is axially mounted on shaft 42 and spun at 600,000 rpm by an imaginary synchronous motor 43.

The circular permanent magnet 40 has a magnetization direction (arrows S-N). A signal coil 208 is mounted stationary to the permanent magnet 40, being wound around but spaced from a soft iron central cylindrical core 40A. The soft iron core 40A is attached coaxially to the rotational axis of permanent magnet 40.

It is very evident that if this permanent magnet where spun at this imaginary speed a rotating magnetic field would exist above the permanent magnet 40. Now since the coil 208 is positioned coplaner to the rotating field no flux linkage will occur and no voltage will be induced in coil 208. In FIG. 9 a rectangular non-ferrous target 44 is postioned in proximity to the face of the spinning magnet 40. This rotating field induces eddy currents in non-ferrous target 44. These eddy currents reduce the flux coupling in the 180 degree azimuth area, thus the flux coupling is greater in the 0 degree azimuth area 46. A 0 degree phase angle signal is generated as indicated in FIG. 9A. In FIG. 10 the rectangular non-ferrous target 44 has moved to the exact center of the permanent magnet 40, and the angular motion of the spinning magnetic field induces eddy currents in non-ferrous target 44. But since the flux lines 46 have been reduced equally in the 180-0 degree azimuth areas, there is no net flux linkage to pick-up coil 41 and no output signal is indicated in FIG. 10A. For a better understanding of this rotating constant flux level and its application to sensing surface geometry refer to FIG. 11 where the imaginary motor 43 is spinning the permanent magnet 40 at 600,000 rpm (this is equivalent to a core sine-cosine excitation of 10 KHZ). In FIG. 11 the non-ferrous rectangular target 47 is inclined at an angle to the face of rotating permanent magnet 40, therefore the nearer 0 degree azimuth portion has greater eddy currents induced than the 180 degree azimuth portion, and thus a 180 degree signal is shown in FIG. 11A. In FIG. 12 there are two non-ferrous targets 48 and 49 that are symmetrically spaced over the face of rotating magnet 40. The equidistant targets 48 and 49 produce a flux symmetry and there is no net linkage to pick-up coil 41, and no signal indicated in FIG. 12A. FIG. 13 shows the same spinning permanent magnet example with a non-ferrous cylinder 50 proximate to, and slightly offset to the 0 degree azimuth of the spinning magnet 40. The non-ferrous cylinder 50 being off-center to the axis of the spinning permanent 40 repels the rotating sensing pattern in the 0 degree azimuth. The greater net flux coupling is in the 180 degree azimuth as indicated by the 180 degree phase angle signal shown in FIG. 13A.

As is evident from this example a rotating constant flux level can be utilized to indicate flux asymmetries. It is believed by the inventor that the preceding analogy represents the rotating magnetic field operation of the polar sensor of the present invention. Of course ferrous metal can be detected, the signal being shifted in phase by 180 degrees.

I will now explain some of the asymmetric sensing fundamentals of the present invention e. g. showing how the polar sensor differentiates between symmetric/asymmetric target surfaces. FIGS. 14–17 illustrate the preferred embodiment of a concave sensing face polar sensor. The pick-up core 107 of the concave sensing face polar sensor has a cylindrical concave shaped sensing face 111 to conform to a cylindrical article. This concave shape provides better flux coupling to the cylindrical article 110. FIG. 14A is a radial (top view) of the concave face polar sensor of FIG. 14 showing pick-up coil 108.

The ferromagnetic pick-up core 107 has a signal coil 108 wound around the central pole, (the leads, etc are not shown for clarity). Since the protruding points 112 and 113 of the cylindrical concave sensing face 111 are the same height and spacing from the central pole, flux symmetry is retained. With no target present as in FIG. 14 the rotating flux pattern is symmetrically balanced and no signal is generated as shown in FIG. 14C. The sine-cosine reference signal is shown in FIGS. 14B, 15B, 16B, and 17B. The concave face pick-up core core 107 is shown in FIGS. 15, 15A. In FIG. 15 a non-ferrous cylindrical article 110 (shown in fragmentary form) is symmetrically positioned above the concave sensing face of polar sensor 107, this balanced flux coupling being indicated by the circular shaded area 109 in FIG. 15A. No signal is shown in FIG. 15C because the flux is 360 degree balanced. If the cylindrical article were formed of a ferrous metal the signal would also be nulled because again the flux would be 360 degree balanced. In FIG. 16 the non-ferrous cylindrical article 110 is tilted at an angle to the concave face of pick-up core 107, in this tilted position the flux being unbalanced as shown by the oval shaded area 109 in FIG. 16A. The eddy currents in non-ferrous target 110 repel the flux coupling toward the 0 degree azimuth and a 0 degree signal is shown in FIG. 16C. In FIGS. 16, and 17 the polar sensor 107 has been arbitrarily rotated in azimuth by 90 degrees as an example so that we can arbitrarily chose any azimuth reference for convenience, if the output signal is properly referenced to that chosen azimuth. In FIG. 17 the cylindrical article 110 is tilted in the opposite angular position causing more flux coupling in the 180 degree azimuth, and thus a corresponding 180 degree signal is shown in FIG. 17C. In FIG. 18 the same components are turned 90 degrees for a different view, (a radial view of the concave sensing face). The sine-cosine reference waveform is shown in FIGS. 18B, 19B, 20B, and 21B. The non-ferrous cylindrical article 110 is in a symmetrical relationship to the pick-up core 107 except for the dented area 114 at the 0 degree azimuth. Dent 114 allows more flux to couple in the 0 degree azimuth area as shown by the shaded area 109 in FIG. 18A. A corresponding phase 0 degree signal is shown in FIG. 18C. FIG. 19 shows the same example arrangement except the dented area is in the 90 degree azimuth area, and the corresponding 90 degree output signal is shown in FIG. 19C. FIGS. 20, 20A show the same example arrangement except the dented area is in the 180 degree azimuth area and the corresponding 180 degree signal is shown in FIG. 20C. FIG. 21 repeats the same example except the dent is located in the 270 degree azimuth area (shaded area in FIG. 21A) and a corresponding 270 degree signal is shown in FIG. 21C.

As is very evident the polar sensor of the present invention transduces much more container surface information than the conventional uniaxial sensor. The dented area is actually resolved into polar coordinates providing theoretically more than 180 times as much information as a bi-axial sensor e.g. due to the 360 degree polar sensing range, having an angular resolution of less than one degree.

DEFINITIONS

Multiple polar sensor assembly: (1) a hollow toroid core having eight polar sensors mounted in bores in the lesser circumference wall. (2) a hollow toroid core having a plurality of polar sensors mounted anywhere in the wall of the core. The mounted polar sensors are for picking up a number of signals simultaneously.

Polar sensor: a single sensing unit comprising a pick-up core with a pick-up coil wound around a central pole, a sensing face, and having a 360 degree polar sensing pattern. Target direction is indicated by phase angle and target distance is indicated by amplitude of the output signal. A hollow toroidal core excited by sine-cosine excitation being necessary to magnetically excite this polar coordinate sensing element.

Pick-up core: a core formed of ferromagnetic material comprising: a cylindrical outer pole disposed concentrically around a central inner pole; these two concentric poles comprising a sensing face. The end opposite the sensing face being connected by means of a base portion, completing the magnetic circuit.

Inspection zone: the band-like sensing area of the eight polar sensors mounted in the inside circumference wall of the hollow toroid core. Two such inspection zones are provided in the present invention.

BRIEF DESCRIPTION OF THE DRAWINGS

FIG. 1 is a perspective view of a hollow toroid core showing the inside and outside windings, and the relative rotational directions of the rotating magnetic field.

FIG. 1A is a cross-section view of the hollow toroid core shown in FIG. 1.

FIG. 2 is a perspective view of a hollow toroid core showing one radial side and also the relative rotational directions of a Z-axis through the two radial side walls.

FIG. 3 is a perspective view of a conical hollow toroid core showing the mounted polar sensors 28.

FIG. 4 is a perspective view of the polar sensor utilized throughout this the present invention.

FIG. 5 is a perspective view of a hollow toroid core having a mounted polar sensor.

FIG. 6 shows the flux path coupling a ferrous target at the face of a polar sensor.

FIG. 7 is a perspective view of a mounted polar sensor illustrating the Z axis of the rotating magnetic field.

FIGS. 8, 9, 9A, 10, 10A, 11, 11A, 12, 12A, 13 and 13A illustrate the principles relating to a constant flux level rotating magnetic field.

FIGS. 14, 14A–14C, 15, 15A–15C, 16, 16A–16C, 17, 17A–17C, 18, 18A–18C, 19, 19A–19C, 20, 20A–20C, 21 and 21A–21C illustrate the asymmetric flux detection principles of the polar sensor.

FIG. 31 is a partially cross-sectional view of the flaw detection apparatus of FIG. 30.

FIGS. 32A–32C illustrate the generation of the eight in-phase signals utilized to determine presence/absence of the inspected container in the inspection zone.

FIG. 32D shows the azimuth reference points assigned to the polar sensor face.

FIG. 34 is a schematic of the parallel connections supplying sine-cosine excitation to the pair of multiple polar sensor assemblies.

FIG. 34A is the 90 degree phase displacement of the pair of multiple polar sensor assemblies.

DETAILED DESCRIPTION OF THE PREFERRED EMBODIMENTS

Figure 9A:
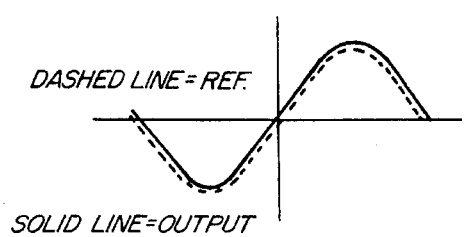
Figure 10A:
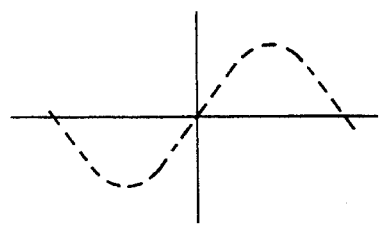
Figure 10:
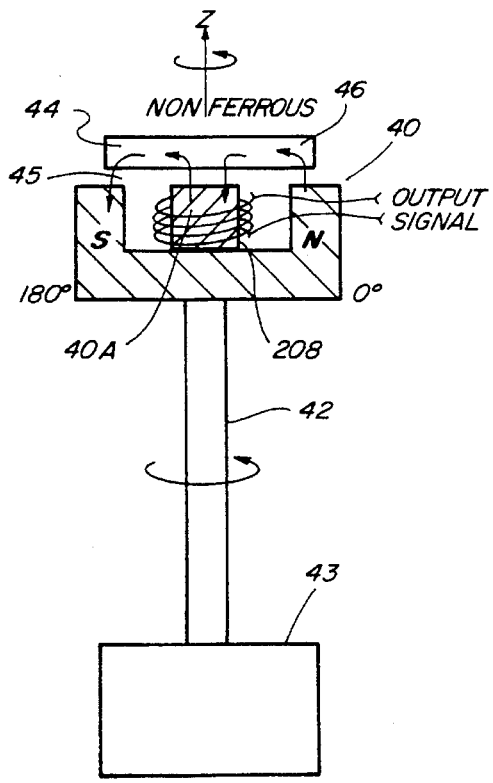
Figure 11:
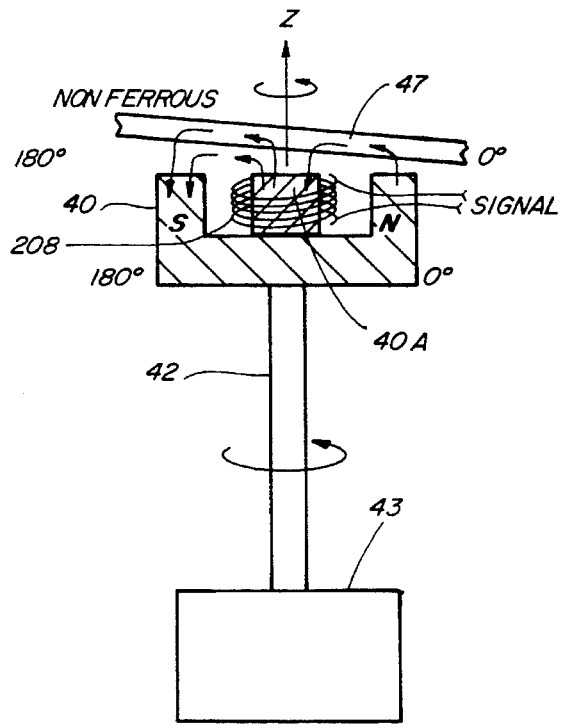
Figure 11A:
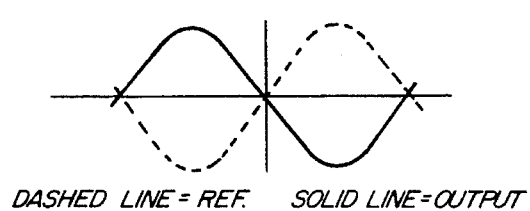
Figure 12A:
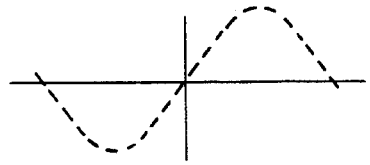
Figure 12:
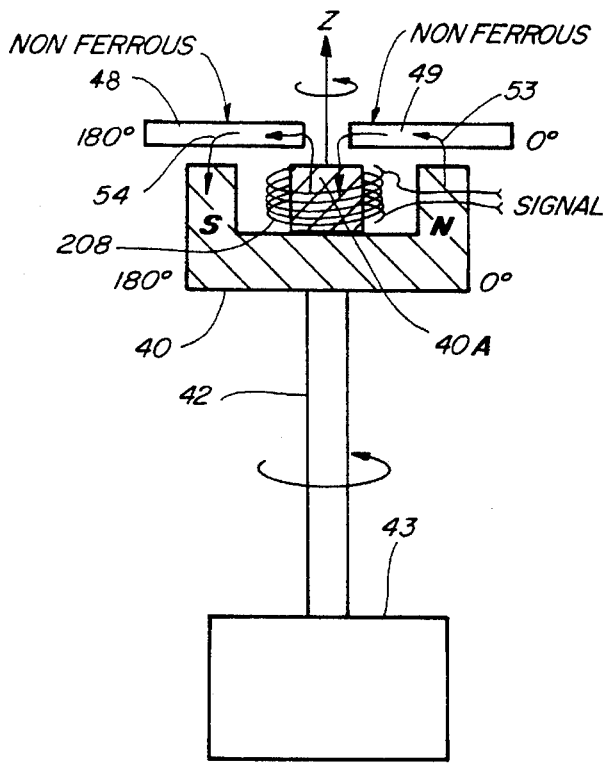
Figure 13:
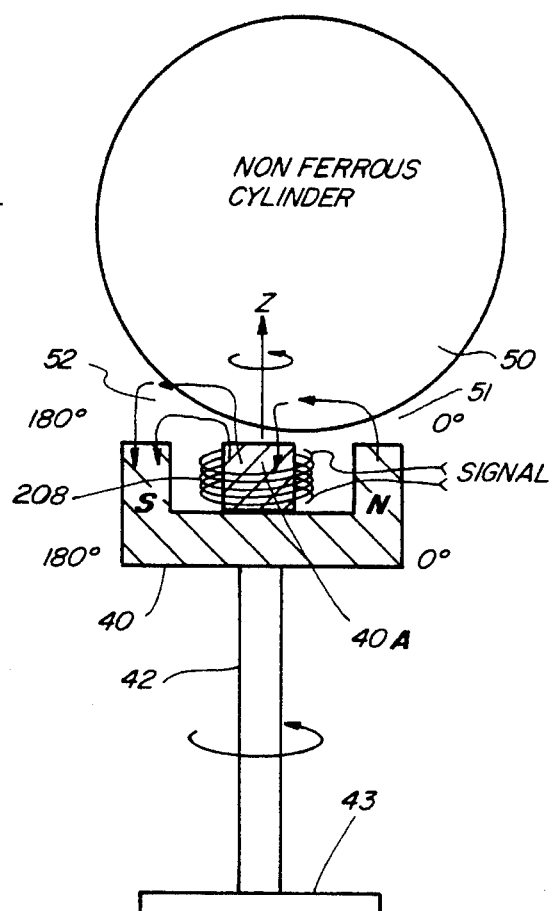
Figure 14:
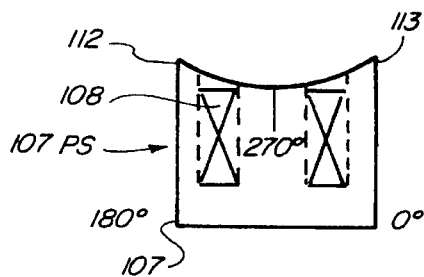
Figure 14:
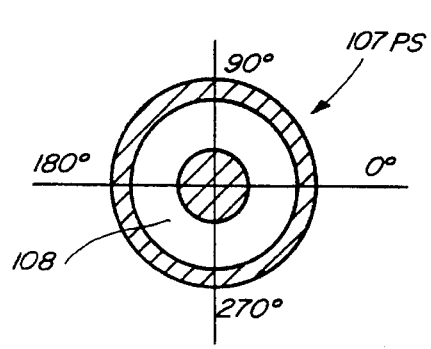
Figure 12:
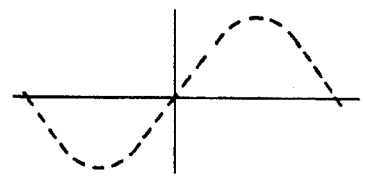
Figure 13:
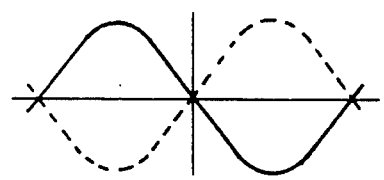
Figure 14B:
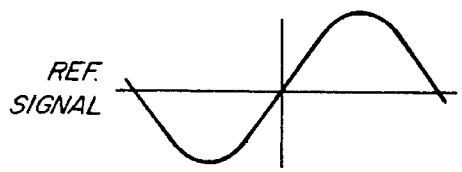
Figure 14C:
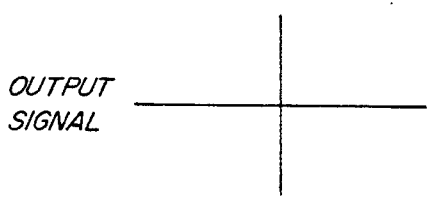
Figure 15:
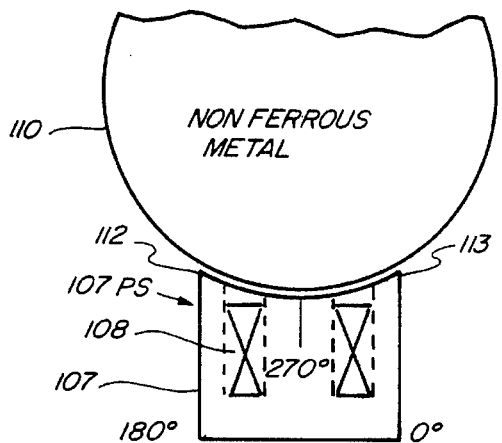
Figure 15B:
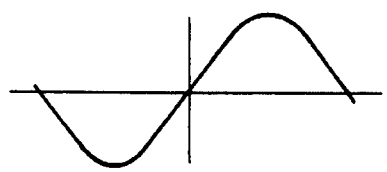
Figure 15A:
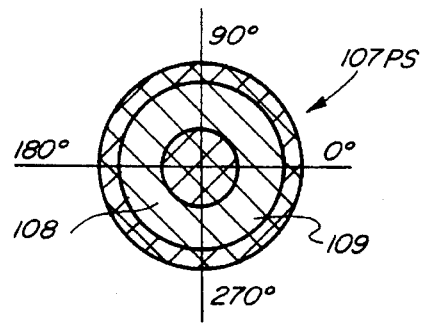
Figure 15C:
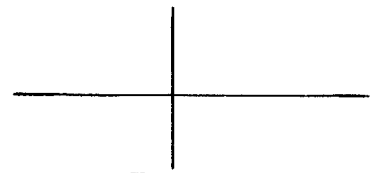
Figure 16:
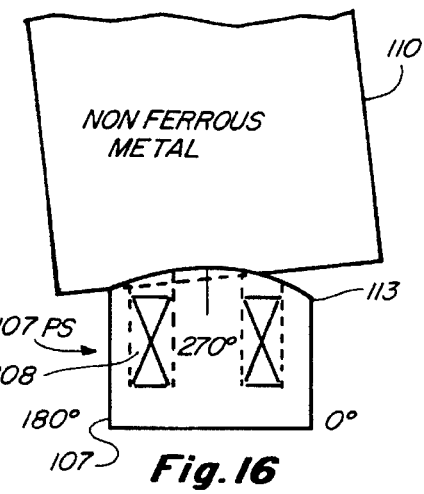
Figure 16A:
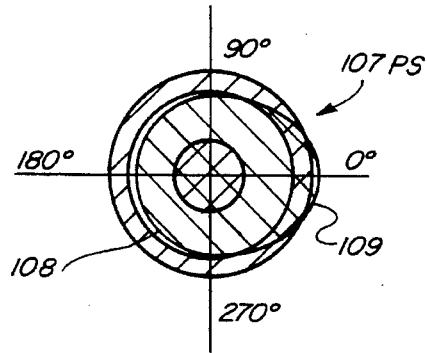
Figure 16B:
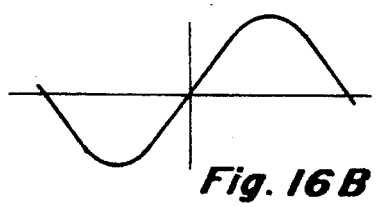
Figure 16C:
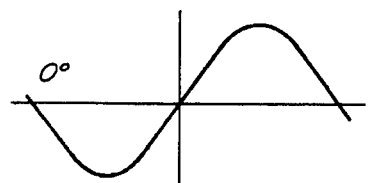
Figure 20:
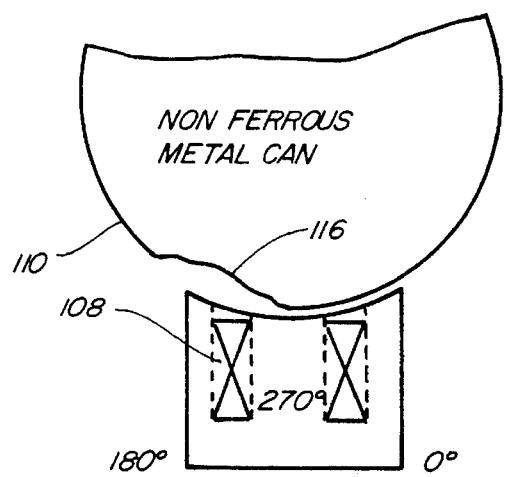
Figure 21:
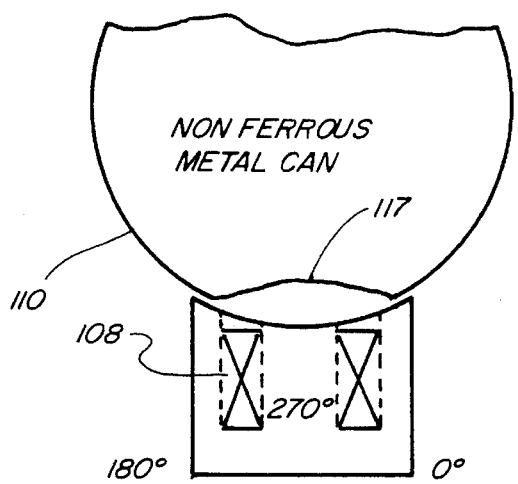
Figure 20A:
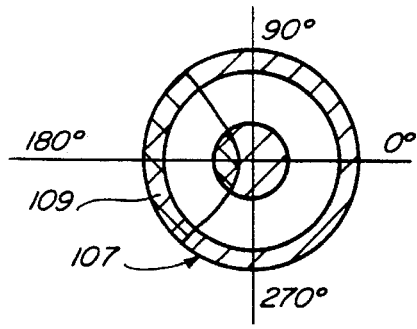
Figure 21A:
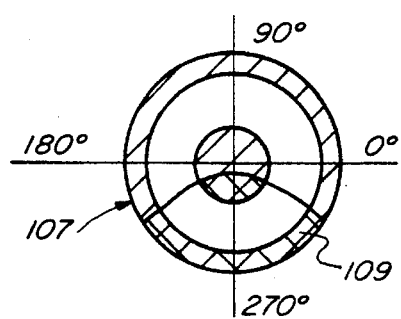
Figure 20B:
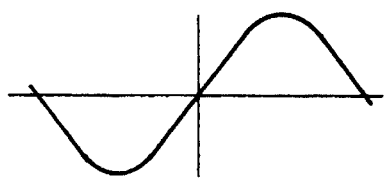
Figure 21B:
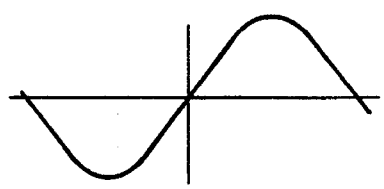
Figure 20C:
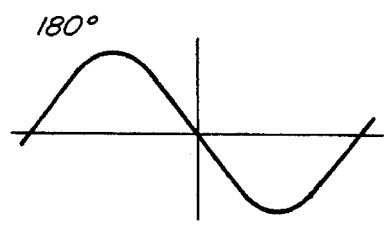
Figure 21C:
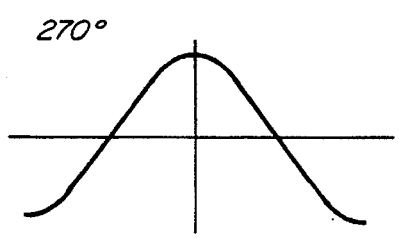
Figure 22:
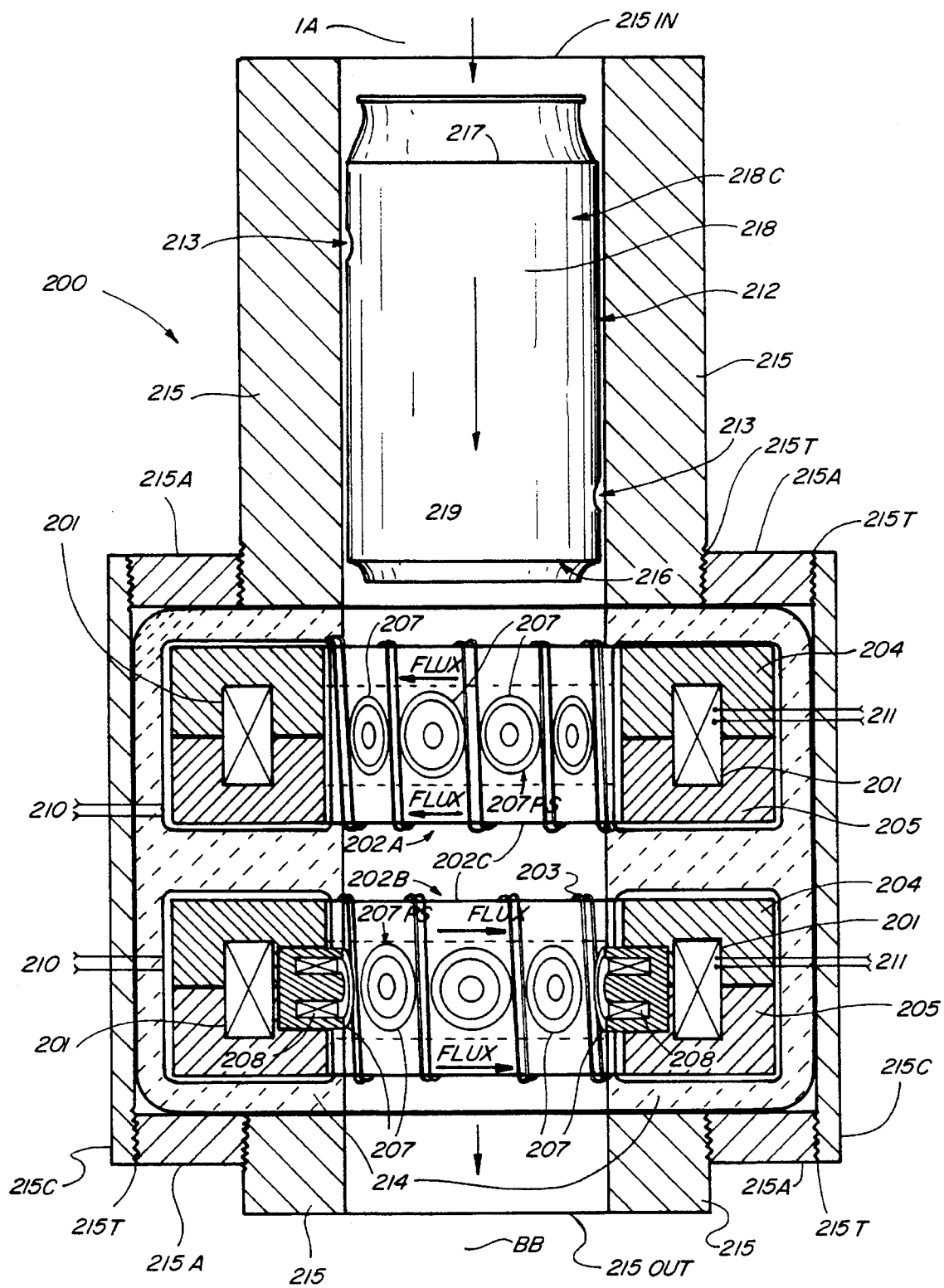
FIG. 22 is a partial cross-sectional elevation view of a multiple polar sensor apparatus for cylindrical article sidewall flaw detection.

Cylindrical article sidewall flaw detection apparatus FIG. 22 illustrates an apparatus 200 for detecting surface flaws such as dents 213 in the surface 218 of a cylindrical object such as an aluminum can body 218C having a central cylindrical axis AA extending between a first axial end 216 and a second axial end 217 thereof. The apparatus 200 comprises an axial guide path assembly 215 which guides cylindrical articles 218C along an article displacement path 219 having a central longitudinal axis BB. The articles 218C are guided along the path 219 with the central longitudinal axis AA of each article aligned coaxially with the longitudinal axis BB of the path 219. The apparatus 200 comprises a pair of identical multiple polar sensor assemblies 202A, and 202B positioned in annular relationship with the displacement path 219. The multiple polar sensor assemblies 202A, 202B generate a plurality of phase/amplitude modulated signals representative of the surface geometry of a cylindrical article 218C which traverses the displacement path 219. As illustrated in FIG. 22, axial guide path assembly 215 may comprise a non-ferromagnetic tubular member 215 which may be aluminum, having an infeed end 215IN, a central cavity 219, and a discharge end 215OUT. The axial path may have an inside diameter slightly larger than the diameter of article 212. Member 215 is preferably grounded to prevent static electricity build-up.

Multiple polar sensor assemblies

Referring again to FIG. 22 the pair of identical multiple polar sensor assemblies 202A and 202B are coaxially aligned with the axial displacement path 219, one above the other. The tubular member 215 is axially divided to make space for this pair of multiple polar sensor assemblies.

The two multiple polar sensor assemblies 202A, and 202B are actually two separate inspection zones, that share the same longitudinal axis, one above the other.

Figure 23:
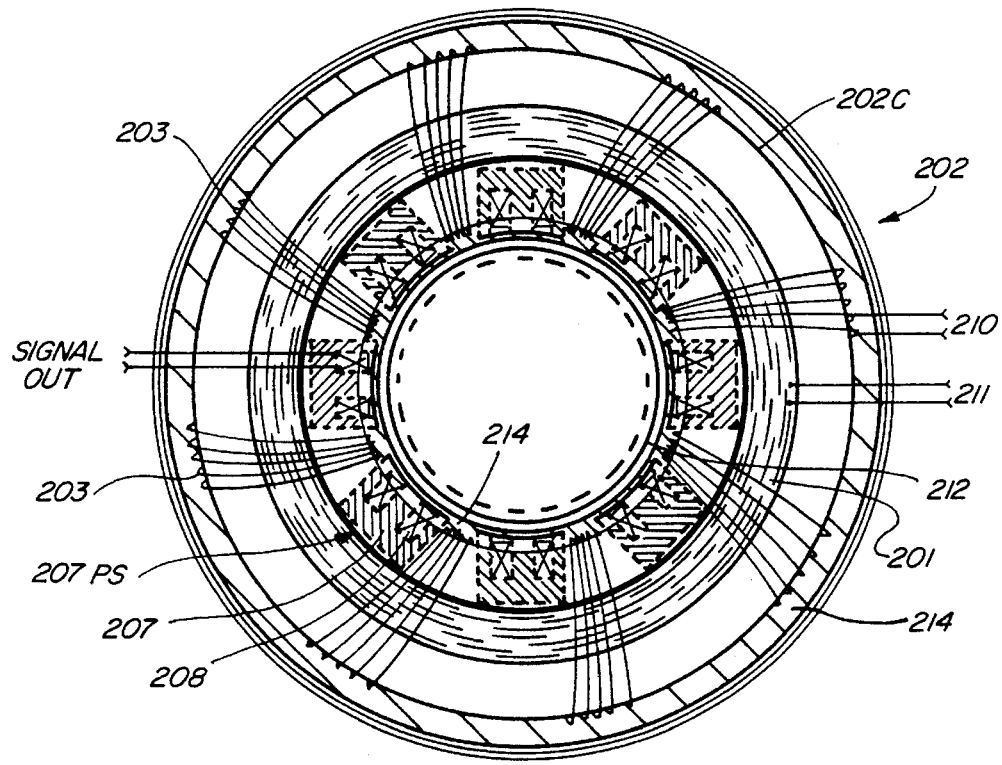
FIG. 23 is a radial view of one assembly of a pair of multiple polar sensor assemblies.

Multiple polar sensor assemblies 202A and 202B are rigidly held in place by means of a high grade non-metallic encapsulant compound 214 this is also seen in FIG. 23. A non-ferrous metal tubular member 215C which helps support the complete structure, and which also acts as a Faraday shield is shown encircling the potting compound 214, tubular member 215C is threaded to the two reducers 215A, which in turn are threaded to tubular member 215. With the multiple polar sensor assemblies 202A and 202B axially positioned in this manner, the inspected containers 218C pass through the center holes of the pair of hollow toroids 202C in a continuous stream. Each of the two multiple polar sensor assemblies 202A and 202B comprise a hollow toroid core 202C formed of ferromagnetic material. The hollow toroid core 202C is separably constructed of two annular grooved halves 204, and 205, providing a toroidal space for the inside excitation winding 201. The inside winding 201, which has connecting leads 211. The outside excitation winding 203 is equally divided into eight coils, and symmetrically wound between the extending portions (the portion of the pick-up core protruding out of the hollow toroid core wall) of mounted pick-up cores 207, and having connecting leads 210. As mentioned the pick-up core element is mounted partially within a bore in the hollow toroid core wall.

Figure 30:
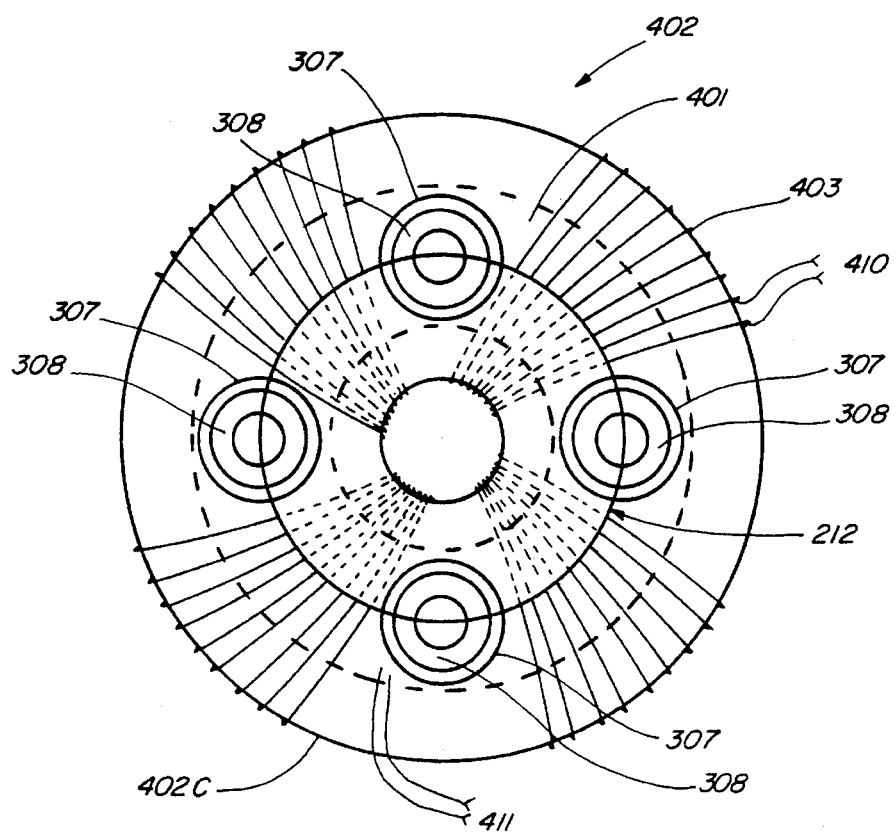
FIG. 30 is a radial view of the second embodiment of a flaw detection apparatus for detecting flaws such as cracks and dents in cylindrical containers

The eight bores in the inside circumference wall of the hollow toroids 202C should be sized so the pick-up cores 207 will fit tightly for good flux coupling all around the pick-up cores 207, and securely glued in place. Each multiple polar sensor assembly 202A, and 202B has eight internal diameter mounted polar sensors 207PS mounted partially within eight bores in the lesser circumference of the hollow toroid 202C, each pick-up core 207 has a signal coil 208 wound around the central pole. The concave face of each of the pick-up cores 207 are aligned in circumference registry with the inspected container 212 as shown in FIG. 30, for better flux coupling. FIG. 23 is a radial view of a multiple polar sensor assembly 202 (same as 202A, 202B) showing the eight mounted polar sensors 207. The outside excitation winding 203 is symmetrically wound between the extending portions (portion of pick-up core 207 extending beyond the surface of the hollow toroid core) of the mounted polar sensors for flux symmetry. The inside excitation winding 201 is shown by dashed lines. The concave sensing faces of the pick-up cores 207 may be seen in FIG. 23. The cylindrical specimen article 212 may be seen concentric to the central axis of the hollow toroid core. The extending portion of the pick-up cores 207 are encased with a thin layer of potting compound 214 for protection from contamination, but still providing a free path for the can stream. In FIG. 22 the arrows labeled FLUX indicate the relative magnetic polarity between the two hollow cores 202C this subtractive polarity is necessary to prevent inducing currents into the can stream, this is better seen in FIG. 34 where the outside excitation windings 203 of multiple sensor assemblies 202A and 202B are connected in subtractive polarity. It will be noted in FIG. 34 that the inside excitation windings 201 are also connected in reverse polarity, the reason for this is to make all sixteen polar sensor fields rotate in the same direction for signal uniformity. The sine-cosine signal generator for supplying excitation to the pair of multiple polar sensor assemblies 202A, and 202B is not shown because these generators are well known in the art. This note also applies to the flange flaw detection apparatus disclosed later in this section.

One additional note, in FIG. 22, the longitudinal relationship between the two multiple polar sensor assemblies 202A and 202B is such that one is angularly offset in relation to the other by 22.5 degrees to provide overlapping coverage of the sixteen pick-up cores 207.

Although the preceding apparatus has been described as a ferrous or non-ferrous can inspection apparatus, it is contemplated that this same cylindrical article flaw detection apparatus can be used to inspect ferrous or non-ferrous tubing or pipe for surface flaws such as dents and cracks. It is also contemplated that solid ferrous or non-ferrous cylinders can be inspected for surface imperfections using the described apparatus. It is also contemplated that this sidewall sensor apparatus may also be utilized to inspect tin an aluminum cans having outside diameter extending seams or flanges. The polar sensor has a greater sensing face to target tolerance than conventional sensors. Also the described apparatus will work in both vertical and horizonal positions as the particular application might require.

Magnetic and electrostatic shielding

Figure 29:
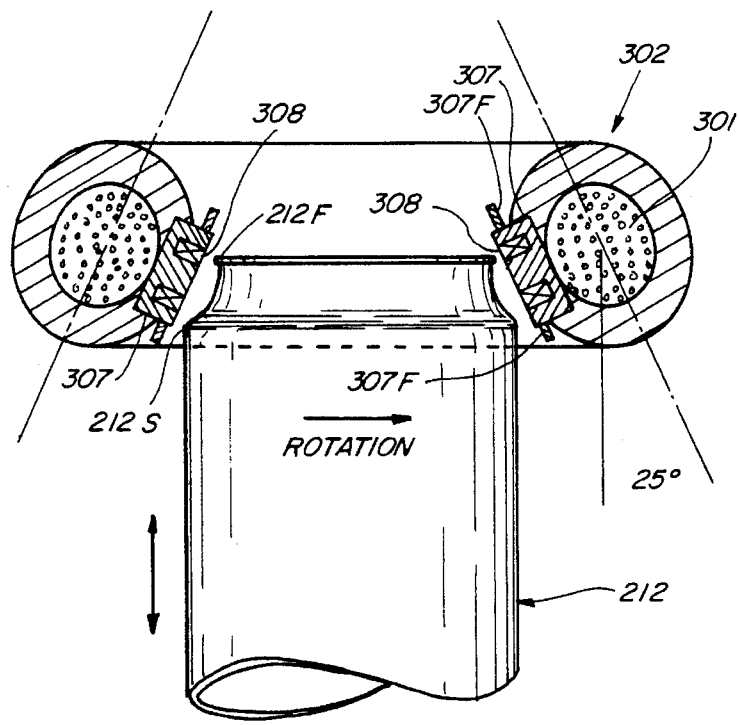
FIG. 29 is a cross-sectional elevation view of the container embodiment of FIG. 28.
Figure 42:
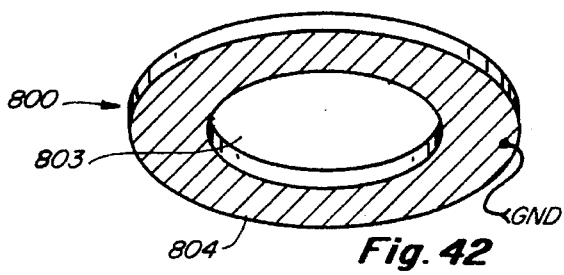
Figure 43:
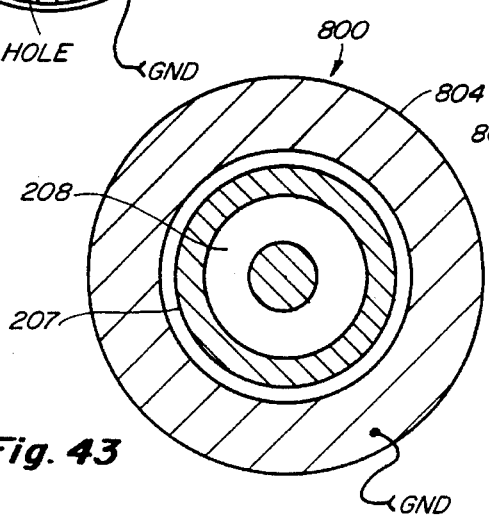

The applicant has found that the surface geometry resolution of the polar sensor can be improved by placing a washer-like non-ferrous shield around the extending portion of the mounted pick-up core. Referring now to FIG. 42 is shown a ring like member 800, formed of a non-ferrous metal preferably copper having a grounding lead labeled GND. By placing this magnetic shield 800 around the extending portion of pick-up core 207 in FIG. 43 (radial view) the background rotating flux leakage from the inside circumference of the hollow toroid core in FIG. 29 is effectively canceled by the opposing eddy currents set up in this: washer like member 800. The use of the magnetic shield 800 has also been found to affect the ferrous signal amplitude by lowering the amplitude of the sensor output signal in response to a ferrous target. It is believed by the present inventor, by selecting the optimum inside/outside diameter ratio 803/804 the ferrous-non-ferrous signal amplitudes can be made equal, this would make the signal amplitude parameter simpler to program into the host computer when changing from aluminum to tin cans.

Figure 41:
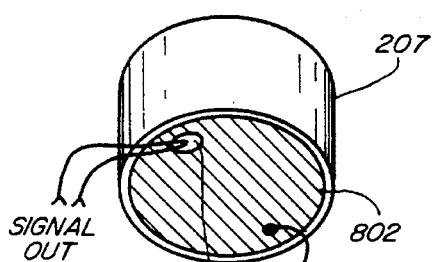
FIGS. 41–44 are showings of magnetic shielding and Faraday shielding used with the polar sensors of this invention.
Figure 44:
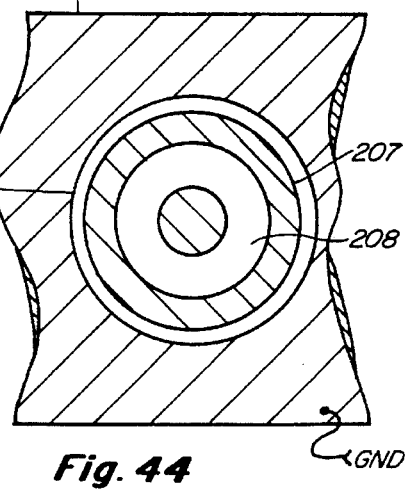

In FIG. 44 is the second embodiment of this magnetic shielding concept in which a cylindrical shaped thick copper foil 801, having eight holes 803A, (only one hole 803a is shown in FIG. 51), this copper foil is formed around the extending portion of each of the eight pick-up cores 207 in FIG. 29, this shield is not shown in FIG. 29 to avoid crowding. It is contemplated that this magnetic shielding could be placed around the extending portion of the pick-up cores 207 as the parts of the multiple polar sensor assembly are assembled. The face of the pick-up core 207 should be approximately even with the edge of the hole 803 of the washer-like member 800. This guideline also applies to the multiple hole embodiment in FIG. 44. This magnetic shielding method has a quasi-focusing effect on the rotating field pattern, which improves the sensor surface contour sensing resolution. The inventor has found that a 5" square sheet of aluminum held over the polar sensor of the present invention, and oriented until a 360 degree signal null is obtained, and then with the aluminum sheet maintaining that same plane, being moved to various quadrants of said sheet; the result is that the signal remains at a 360 degree null. In FIG. 41 the pick-up core 207 is shown in a rear view angle, showing the Faraday shield 802 glued to the back of the base portion, and having grounding lead labeled GND. This measure prevents noise pick up near the signal coil. These magnetic and electrostatic shielding methods also equally apply to the two disclosed container flange flaw detection apparatus embodiments, in FIGS. 28, 29, 30, and 31.

Also shown in FIG. 41 is a HOLE in the base portion of the pick-up core 207 to provide access to the pick-up coil for connection leads. The two coil leads should be in shielded leads.

The shielded twin leads from each pick-up coil may be routed through the hollow coil space of the hollow toroid core and from there through a hole, or holes to the outside.

Signal processing and software for multiple sensor assemblies

Figure 32:
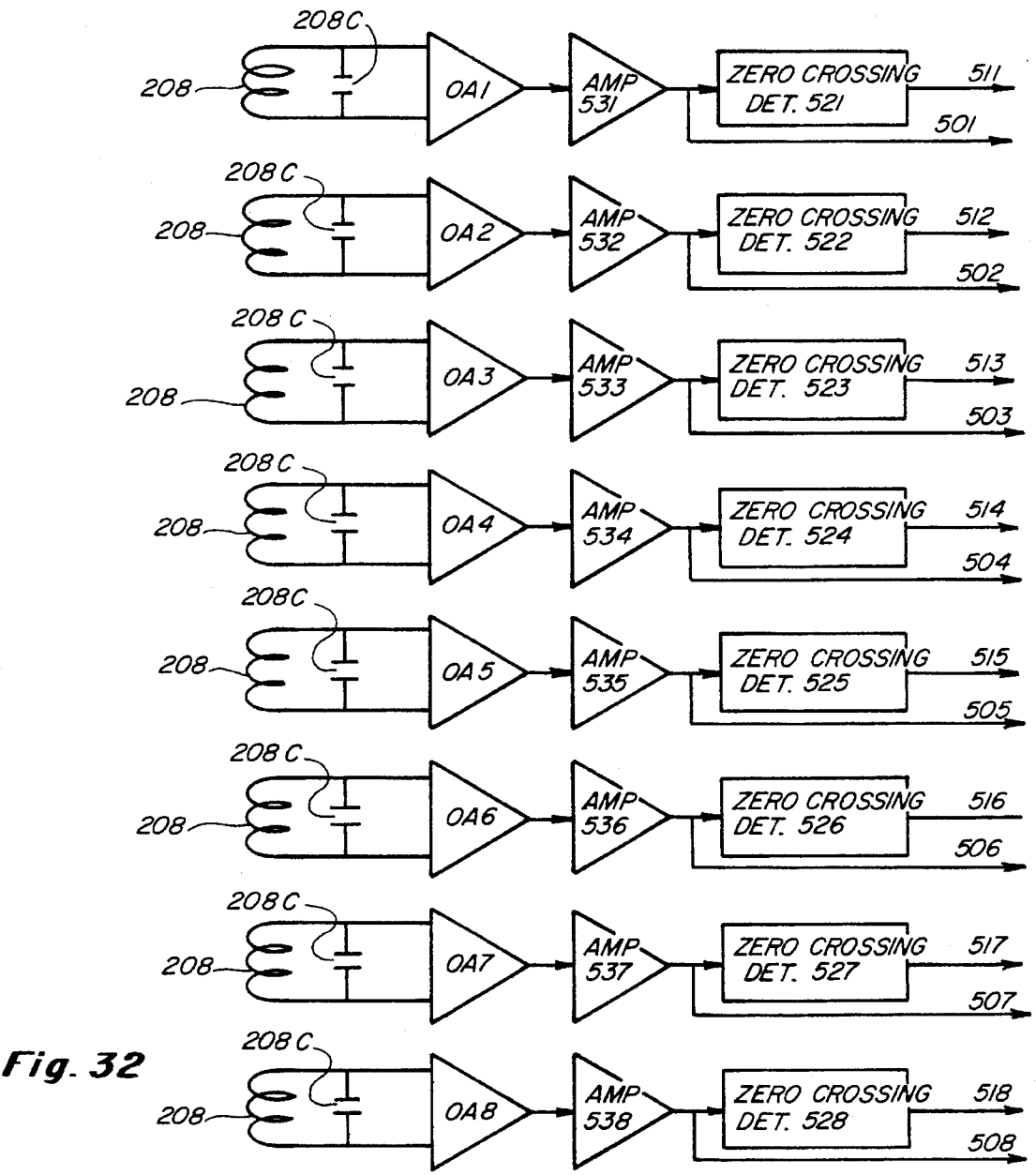
FIG. 32 is a block diagram of one of a pair of multiple polar sensor amplification systems, with zero crossing detection circuits to process polar sensor signals.

Referring now to the preferred pre-amplifier circuit for each of the two groups of eight polar signals, in FIG. 32 is shown eight of the total of sixteen pick-up coils 208, each being connected to a high gain differential op-amp OA1–OA8, all being identical.

Differential amplifiers are the preferred pre-amplifier stage because of their high CMRR.

Figure 33:
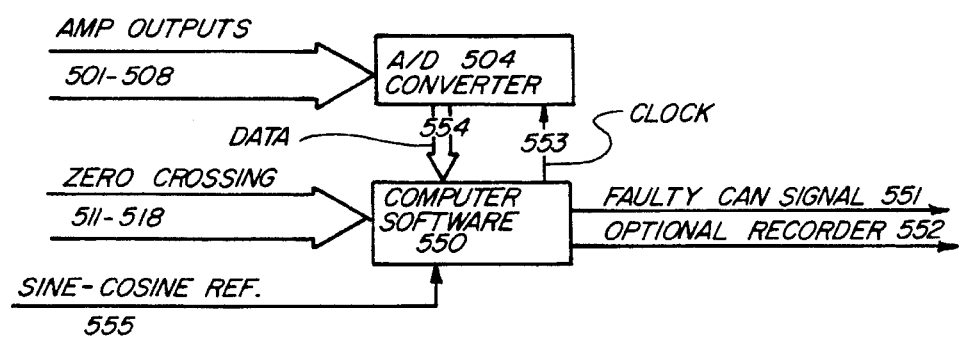
FIG. 33 is a block diagram of one of a pair of multiple signal processing circuits.

This same pre-amplifier, and signal processing are to be used with the other multiple polar sensor assembly, only one is shown here to avoid repetition. In the following description only one pick-up signal path will be described because all sixteen are identical. Each pick-up coil 208 has a capacitor 208C connected across the coil, by selecting the proper capacitance for resonance a higher signal is provided. The OA1 output is connected to the amplifier 531, which acts as a slectable gain stage. This slectable gain stage is used to customize the gain to a particular type of container (ferrous-non-ferrous etc.). From amplifier 531 the amplified signal is applied to the zero crossing detector 521 for extracting the phase angle, the output of this stage is fed on line 511 to the computer software 550 in FIG. 33, more about how the phase angles are processed in the computer, to produce the container presence/absence signals later in this section. From amp 531 the amplified signal is also fed by line 501 to the A/D converter in FIG. 33. A/D converter 540 may be two eight channel analog/digital converters such as Analog Devices 8-channel, 12 bit parallel data acquisition system AD7890 or AD7891, these A/D converters are given only as perspective examples, as other signal processing circuits are known in the art. In FIG. 33 the A/D converter 540 is connected to the computer 550 by data bus 554, also clock signals are fed from the computer 550 to converter 540 by line 553. The outputs of amps 531–538 are also fed to the computer 550, for flaw signal processing, a sine-cosine excitation reference signal 555 is also fed into the computer for phase demodulating.

To explain the software programming of the article presence-absence signals, refer now to FIGS. 32A, 32B, and 32C. As has been mentioned the sixteen composite signals picked up by the polar sensors, contain integral components that can be utilized to generate signals indicating to the computer the presence of an article in the inspection zone of each of the first and second multiple polar sensor assemblies 202A, and 202B.

Figure 39:
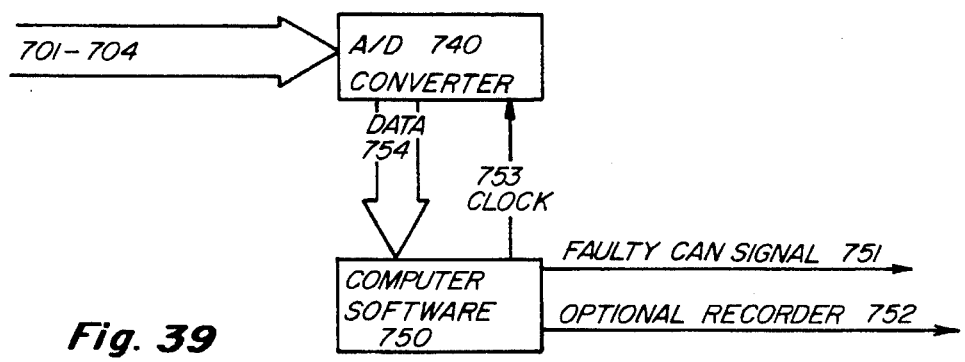
FIG. 39 is the signal processing means for the second embodiment of a flange flaw detection apparatus.
Figure 40:
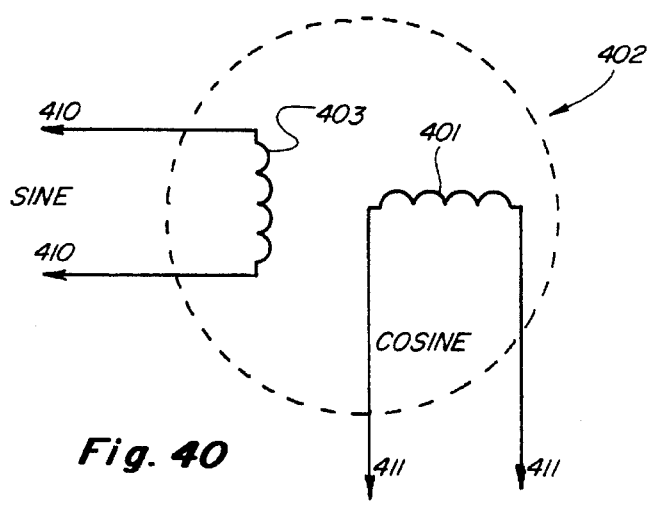
FIG. 40 and 40A show a sine-cosine schematic for the detector of FIG. 30 and the sine-cosine waveforms, respectively.
Figure 40A:
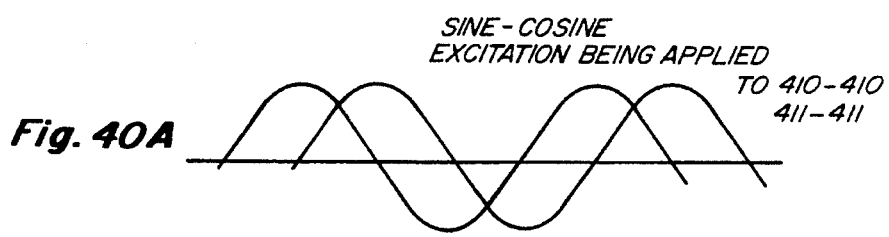

In FIG. 39A a portion of the non-ferrous container 212 is shown [the hatched area], the leading edge 212LE is absorbing the flux in the 90 degree azimuth, (FIG. 39D shows the azimuth reference positions) therefore there is more flux coupling to all eight polar sensors 208 in the 270 degree azimuth area, thus each polar sensor is generating a 270 degree signal, as the can enters the inspection zone. Thus it is conceivable that the host computer can be programmed to process these eight coincidence phase signals to indicate the entrance of the can into the inspection zone. The longitudinal degrees 0–315 correspond to the positions of the polar sensors mounted in one of the multiple polar sensor assemblies 202A or 202B. In FIG. 32B each of the eight polar sensors 208 are in flux symmetry (unless there is a dent in the inspection zone) therefore all eight polar sensors are nulled. Of course the instant all eight polar sensors null to zero the software interprets this to mean the inspection process can begin inside that multiple polar sensor assembly. In order to prevent a dent in the shoulder of the can being interpreted as a broken coincidence signal, the software can be programmed to respond to seven 270 degree coincidence signals instead of eight. Or the alternative, the mentioned irregular shoulder signal can be processed as a flaw signal, which it is. With the computing power of the state of art industrial computers, this should be a small task. Referring now to FIG. 32C the can 212 has moved down with the trailing edge 212TE absorbing energy in the 270 degree azimuth area. All eight polar sensors are coupling flux in the 90 degree azimuth and each producing a 90 degree signal. These eight coincidence signals may be processed by the computer to indicate the end of the inspection process in that multiple polar sensor assembly. Since there are two multiple polar sensor assemblies, thus in essence two inspection zones, the eight signals from each of the multiple polar sensor assemblies are to be processed separately. By means of the above described coincidence signal processing all auxiliary container presence/absence sensors such as light beams etc. can be eliminated and a continuous touching stream of inspected cans may be realized. Also in FIG. 33 the computer software 550 has a faulty can output signal 551, this signal needs to be delayed until the faulty can travels to the ejection zone, this may be accomplished by means of a count procedure programmed into the software. It is to be understood that the present invention is not intended to be limited to the example signal processing circuits given in this section but that other circuits may come to mind to those skilled in the art without departing from the spirit and scope of the present invention.

Container end flange flaw detection principles

In the manufacturing process of aluminum and tin cans, the flange portion of the can must be inspected for cracks and dents before the end panel is attached.

Disclosed now is a rotating magnetic field sensor assembly for detecting flaws such as cracks and dents in the flange portion of aluminum or tin cans.

In order to better understand how the polar sensor of the present invention can sense flaws in the flange of a metal container, refer now to FIGS. 24–27.

Figure 24:
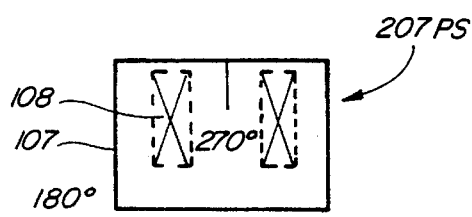
FIGS. 24, 24A–24C, 25, 25A–25C, 26, 26A–26C, 27, and 27A–27C illustrate crack detection utilizing a polar sensor.
Figure 24B:
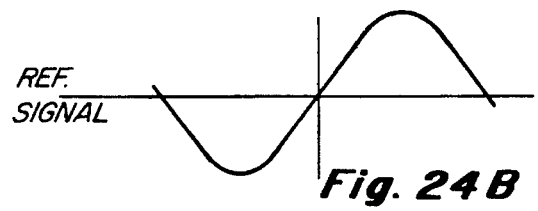
Figure 24A:
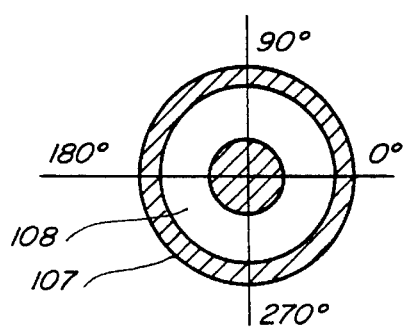
Figure 24C:
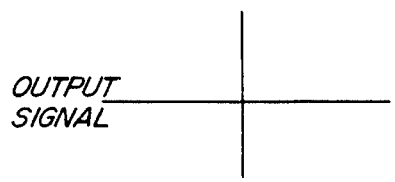
Figure 25:
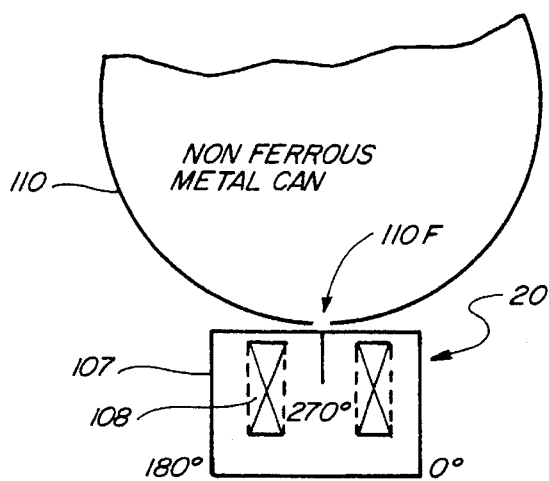
Figure 26:
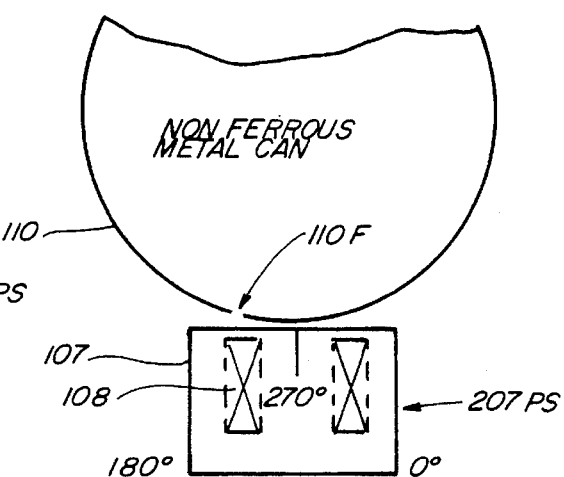
Figure 25A:
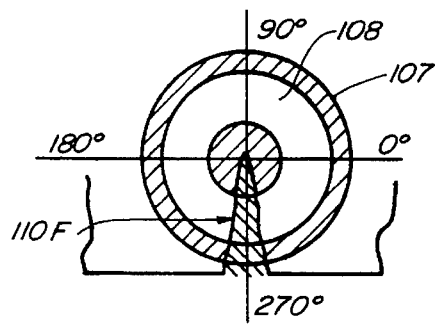
Figure 26A:
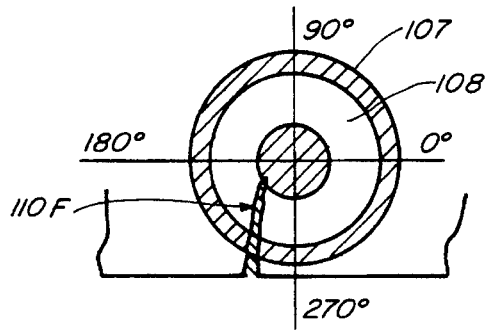
Figure 25B:
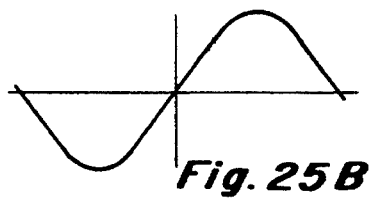
Figure 26B:
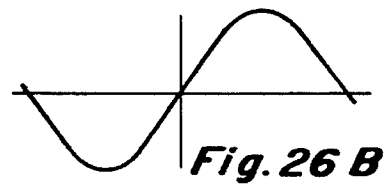
Figure 25C:
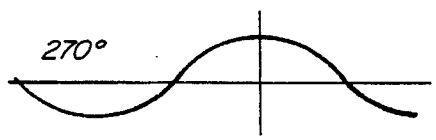
Figure 26C:
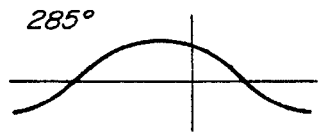
Figure 27:
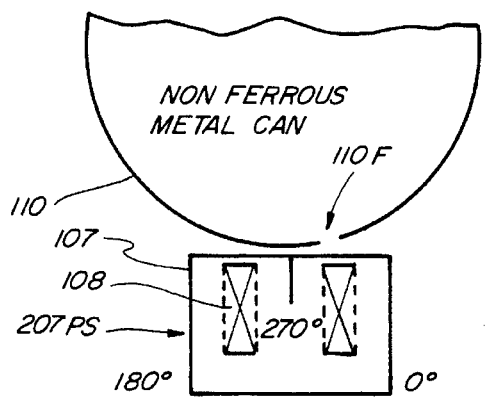
Figure 27B:
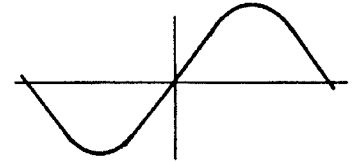
Figure 27A:
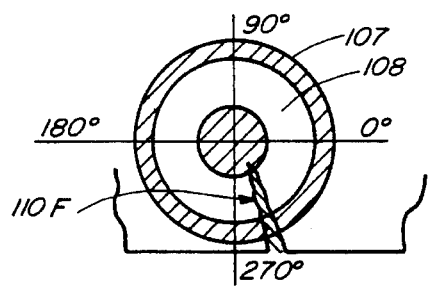
Figure 27C:
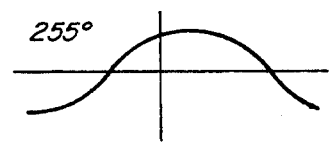

FIG. 24 shows a planar faced polar sensor 207PS. In FIG. 24 there is no target present above sensing face of pick-up core 107, even with no target present the rotating flux has an inherent balance, due to the symmetrical geometric of the pick-up core 107 as seen in FIG. 24A. This inherent circular flux symmetry allows no flux linkage and no voltage is induced as indicated on the output reference line of FIG. 24C. FIG. 25 shows a non-ferrous can body 110 centered above the pick-up core 107, the crack 110F in the flange of container 110 is centered over the 270 degree radial line as seen in FIG. 25A (radial view of the sensing face). The crack 110F causes a small decrease in the eddy currents in the 270 degree azimuth area of pick-up core 107 effecting a small flux asymmetry in the 270 degree area, thus producing a small flux linkage to signal coil 108, and a small 270 degree signal is shown in FIG. 25C. In FIG. 26 there is a crack 110F in the flange of non-ferrous container 110 also shown in FIG. 26A. The flaw 110F is positioned over the 285 degree area of pick-up core 107 thus a 285 degree signal is shown in FIG. 26C. FIG. 27 shows the same positional set-up except the flaw is in the 255 degree radial position as indicated in FIG. 27C. From this reasoning if the cracked flange of a container were rotated on its axis as shown in FIGS. 25–27 the signal phase angle would shift from 270 to 255 degrees.

Figure 28:
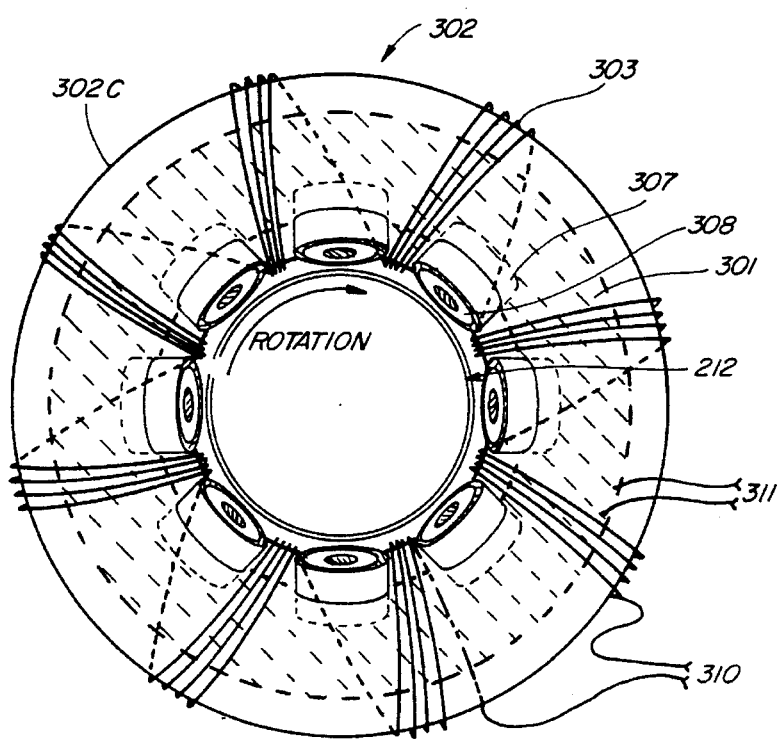
FIG. 28 is a radial view of the first embodiment of a container flange inspection apparatus.
Figure 35:
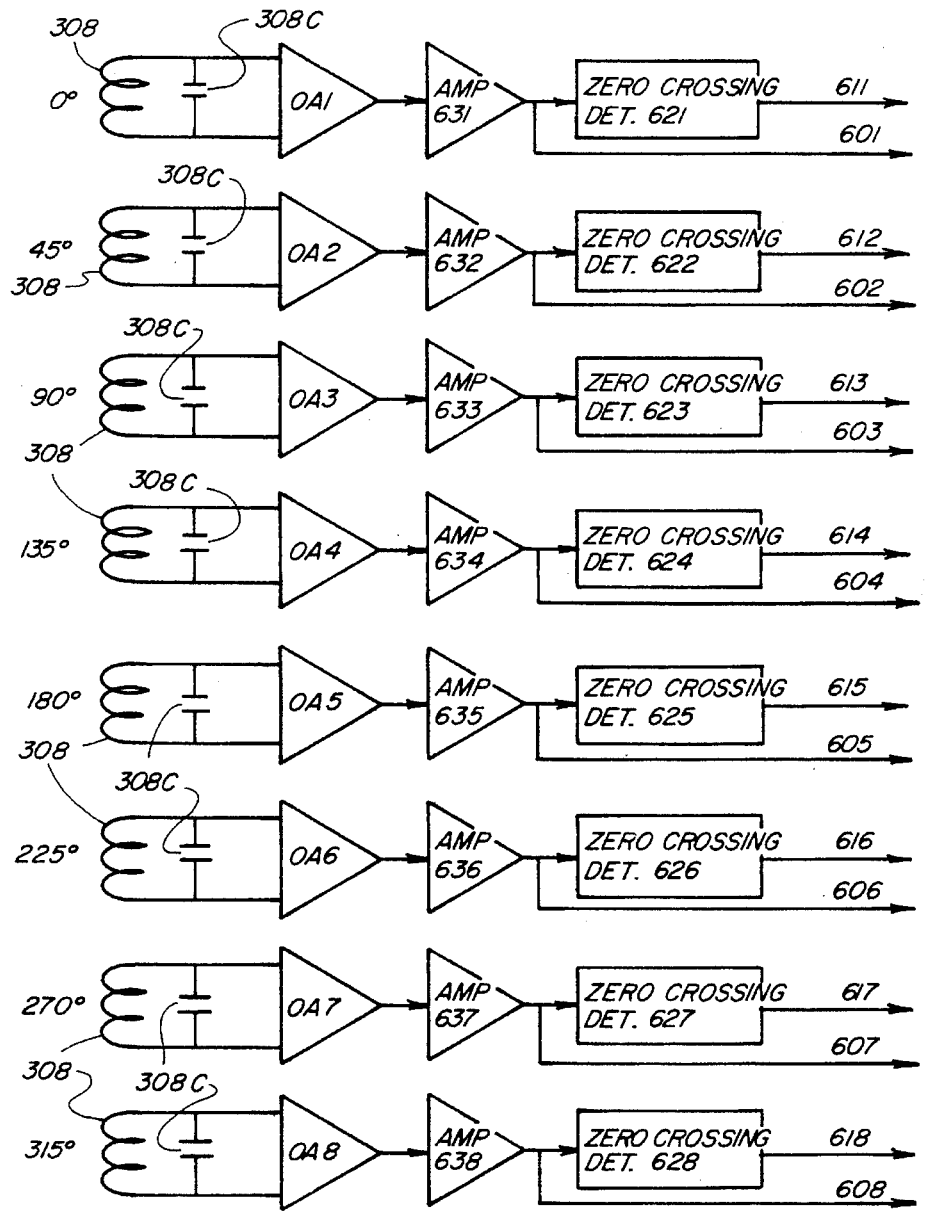
FIG. 35 is the amplification stages for the multiple polar sensor assembly of the first embodiment of a cylindrical container flaw detection apparatus.
Figure 36:
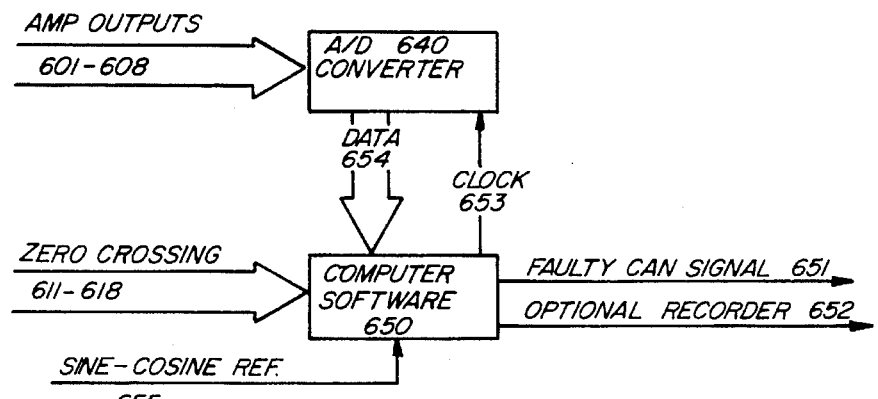
FIG. 36 is the signal processing means for the first embodiment of the cylindrical container flange flaw detection apparatus.
Figure 37:
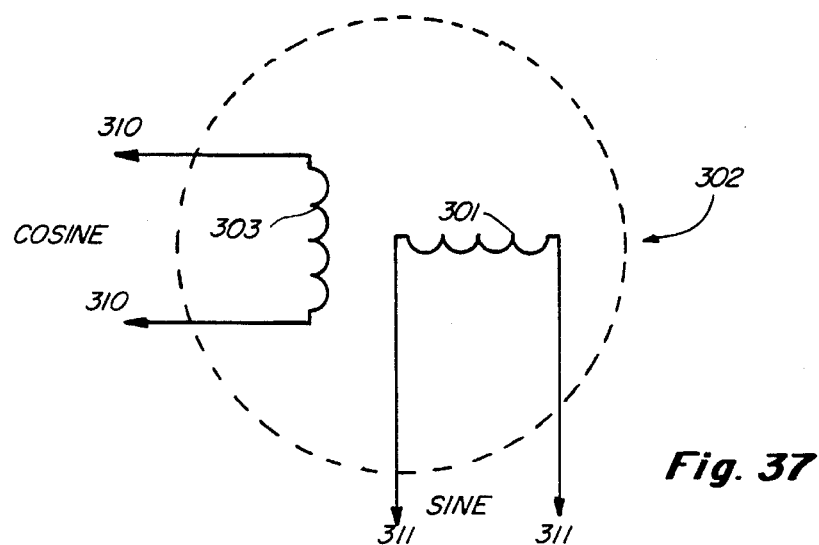
FIG. 37 is a sine-cosine excitation schematic for the apparatus of FIG. 28.

First and second embodiments of cylindrical container end flange flaw detection apparatus Shown in FIGS. 28, and 29 is the first embodiment of a multiple pick-up flange flaw detection apparatus, for sensing cracks or dents in the flange portion of aluminum or tin cans. In FIGS. 28, and 29 only the multiple polar sensor assembly 302 and a portion of the inspected can 212 are shown, the can conveying system is not shown because these are well known in the art. In FIG. 28 the hollow toroid core 302C formed of ferromagnetic material has an inside excitation winding 301, and an outside excitation winding 303 wound around the outside at eight equally spaced positions. When sine-cosine excitation is applied to windings 301 and 303 a rotating field is induced throughout the hollow toroid core. FIG. 36 is a crass sectional view of the hollow toroid 302C, it will be noted the hollow core 302C has an elliptical shaped cross-section. It will also be noted the major axis of the ellipse is angled approximately 25–35 degrees to the axis of the hollow toroid 302C forming a conical inner diameter thereby. The reason for this angular conical shape becomes apparent in FIG. 36 where the face of the pick-up cores 307 are disposed adjacent both the flange 212F and shoulder 212S of container 212. With the pick-up cores 307 angled in this way and container 212 positioned in the cone formed by the circle of pick-up cores 307, a flux balance registry can be attainted, and a perfect flange and shoulder produce a near null signal. This conical arrangement provides simultaneous inspection of both the flange 212F and the shoulder portion 212S of container 212 by utilization of flux symmetry. With a proper level of signal amplification even a small flux imbalance caused by a crack, or dent in the flange or shoulder portion of the inspected container is detected as a phase shift signal, that can vary as widely as 180 degrees, FIG. 35 is a radial view of can 212 showing how container 212 can be rotated for complete coverage.

The container 212 may be rotatably held in coaxial alignment registry with the conical circle of polar sensors, by means of a chuck, or partially surrounded by alignment rollers, many such devices should come to mind to those skilled in such mechanical rotational arts. If the flange 212F and shoulder 212S portions of the inspected can are perfectly concentric (having no dents or cracks) and the can is rotated in near perfect concentric alignment with the conical circle of polar sensors then the output signals will be zero, or all eight signals will have coincidence phase angles, and equal amplitudes.

The host computer may be programmed to detect any phase deviations, and generate a reject signal. It is contemplated that flange presence/absence in the inspection zone may be derived from the null/phase coincidence of all eight polar sensors, by programming this into the host computer.

It will also be noted in FIG. 28, the pick-up cores 307 are mounted in bores at an angle for flux balance registry of each of the eight pick-up cores 307. It is also contemplated that the multiple polar sensor assembly 302 can be encapsulated in a rigid non-metallic potting compound forming a cylindrical casing. A non-ferrous tubular member may surround this cylindrical casing for mounting purposes, and Faraday shielding.

Shown in FIG. 30 is the second embodiment of a container end flange flaw detection apparatus. FIG. 30 is a radial view of hollow toroid 402 showing the inside excitation winding 401, having connecting leads 411, this winding is also seen in FIGS. 31. In this embodiment the pick-up cores 307 are mounted partially within bores formed in one flat radial side of hollow toroid core 402. The axis of these four bores are parallel to the axis of the hollow toroid core. These four bores should also be centered over the inside excitation winding 401 for best flux linearity and coupling. The outside excitation winding 403 is wound around the outside at four equally spaced positions, between the extending portions of the pick-up cores 307, having connecting leads 410. In FIG. 31 the can 212 is shown with the flange 212F in the downward position, to illustrate that this embodiment can be used in any position., horizonal, or vertical. Reference number 110F represents a flaw in the flange portion.

As in the can sidewall detection apparatus the hollow toroid core of this embodiment may be encapsulated in a rigid non-metallic potting compound for mounting and protection.

The container transport system is not shown in FIGS. 30, and 31 because these are well known in the art.

With the container 212 centered over the pick-up cores 307, the container 212 is rotated at least 90 degrees for complete sensing coverage. As in the first embodiment of FIGS. 28, and 29 if the container flange is perfectly concentric, without dents or cracks, and rotated in near perfect axial, and radial alignment the phase of the four output signals from the four polar sensors will be in coincidence, and have equal amplitudes.

Signal processing of flange flaw signals

Figure 38:
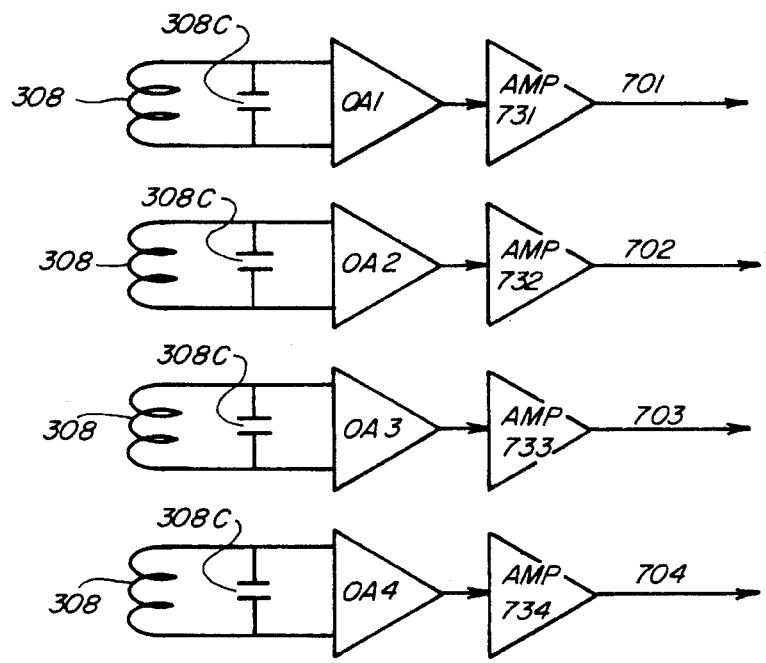
FIG. 38 is the multiple polar signal amplification stages for the second embodiment of a flange flaw detection apparatus.

FIG. 35 shows a multi-signal amplification circuit that may be used with the flange and shoulder flaw detection apparatus of 2FIGS. 28, and 29. The circuit in FIG. 35 is the same as in FIG. 32, only the reference numbers are different. Again each polar sensor generates a phase/amplitude signal representing the flux balance between the flange and shoulder portions of the inspected container 212. These eight signals 601–608 are fed into the A/D converter 640, this A/D converter may be an Analog Devices unit such as AD7890 or AD7891. From the A/D converter 640 the data path is 654 to the computer and software 650 for processing, also comparing the zero crossing signals 611–618 two determine the polar phase angle. By utilizing the phase angle component of these eight signals a plurality of coinciding phase angles may be utilized to indicate the entry of the can 212 into the proper inspection zone, in this way container presence/absence signals may be produced by the computer and software 650. A faulty can signal may be produced on line 651 for removing the defective container from the assembly line. Also an optional recorder signal may be produced on line 652. FIG. 36 is a schematic of the sine-cosine winding for multiple polar sensor assembly 302 of FIG 28. The sine-cosine signals may of course be exchanged to suit convenience, of phase rotation processing. FIG. 30 shows the four differential amplifiers OA1–OA4 which are feeding amplifiers 731–734 from here the signals are fed to the A/D converter 740. In the embodiment of FIG. 30, and 31 the signals 701–704 are fed directly to the A/D converter 740, from 740 the digital data is fed by link 754 to the computer and software 750 for processing, and the faulty can signal will appear on line 751 and the optional recorder signal on line 752. The sine-cosine schematic for the multiple polar sensor 402 is shown in FIG. 38.

The sine-cosine operating frequency of the three disclosed apparatuses has been 12 KHZ in the prototypes the applicant has tested, but it is believed even better results will be obtained with higher frequencies.

While the illustrative and the presently preferred embodiments of the invention has been described in detail herein, it is to be understood that the inventive concepts may be otherwise variously embodied and employed and that the appended claims are intended to be construed to include such variations except insofar as limited by the prior art.

What is claimed is:

1. Apparatus for detecting surface flaws in ferrous or non-ferrous cylindrical articles having central longitudinal axes, comprising:

a) guide means for guiding said cylindrical articles along a displacement path having a central longitudinal axis extending coaxially of said central longitudinal axes of said articles: and a pair of first and second multiple polar sensor assemblies, each disposed coaxially with said displacement path providing first and second inspection zones displaced axially in said displacement path, also each multiple polar sensor assembly generating a plurality of phase-amplitude modulated signals representive of the surface geometry of said article, each multiple polar sensor assembly comprising:
    i) a hollow toroid core formed of ferromagnetic material having a plurality of bores in the lesser circumference wall of the hollow toroid core, the axes of said bores being disposed on a plurality of radial lines perpendicular to the central axis of the hollow toroid core, the central axis of the hollow toroid core being disposed coaxially with the central longitudinal axis of the said displacement path;
    ii) a plurality of polar sensors mounted partially within the bores so as to provide an extending portion outside the surface of the hollow toroid core, each mounted polar sensor coupling a rotating magnetic field to the cylindrical article sidewall to induce eddy currents therein;

iii) each polar sensor generating a phase-amplitude modulated signal representative of a specimen flaw;

iv) a first excitation winding wound within the hollow toroid core for inducing a first magnetic field throughout the hollow toroid core, said first excitation winding having connecting leads;

iv) a second excitation winding wound around the outside of the hollow toroid core, being subdivided and wound between the extending portion of the mounted polar sensors, for flux symmetry, said second excitation winding for inducing a second magnetic field throughout the hollow toroid core;

v) sine-cosine excitation being applied to said first and second excitation windings to induce a rotating magnetic field throughout the hollow toroid core, the said rotating magnetic field having distributive axes perpendicular to the surface of the hollow toroid core everywhere;

vi) the hollow toroid core being separable for assembly;

vii) Faraday shielding surrounding a portion of the hollow toroid core, said shielding being grounded;

viii) signal processing means for receiving said plurality of signals to extract flaw components.

2. The invention of claim 1, wherein each of the said polar sensors comprises;

a) a pick-up core formed of ferromagnetic material further comprising:

i) a central cylindrical magnetic pole, a concentrically cylindrical outer magnetic pole provided around said central magnetic pole and concentrically spaced to provide a pick-up coil space, and a base portion for connecting these magnetic poles at one end, the end opposite the base portion forming an annular sensing face, said face being perpendicular to the axis of said central and cylindrical outer magnetic poles, said pick-up core being mounted partially within the wall of said hollow toroid core with the annular sensing face inward toward the cylindrical article for flux coupling to the cylindrical article sidewall;

ii) Faraday shielding attached to back side of the said base portion, and having a grounded lead;

iii) a pick-up coil wound around the said central cylindrical pole, and having connecting means leading out through a hole in the base portion;

iv) a non-ferrous washer-like magnetic shield disposed concentrically around the extending portion of said mounted polar sensor for shielding the hollow toroid core flux leakage.

3. The invention according to claim 2, wherein the said pick-up core, further comprising:

a concave sensing face for conforming to the cylindrical geometry of the cylindrical article specimen, for better flux coupling.

4. The invention according to claim 1, wherein the said signal processing means further comprises:

a) means to receive and amplify the said plurality of phase-amplitude modulated signals to a suitable level for extracting flaw components, each signal being further processed by:

i) a peak-detector to determine amplitude level, indicating an asymmetric flux coupling to sensing face;

ii) a zero-crossing detector to detect signal phase angle determining the azimuth position of the said asymmetric flux coupling to the sensing face of the polar sensor for indicating flaw location;

iii) software to set an unacceptable signal amplitude level corresponding to the degree of specimen flaw, and also to generate flaw azimuth heading data;

iv) the software also being compatible with the signal phase difference between ferrous and non ferrous specimens.

5. The invention according to claim 1, wherein the said signal processing means, further comprising:

a) suitable circuitry for:

i) detecting a first predetermined coincident phase angle from the polar sensors, representing the leading edge of the cylindrical article in the inspection zone;

ii) detecting a null signal from each of the polar sensors representing the cylindrical article within the inspection zone;

iii) detecting a second predetermined phase angle from the polar sensors, representing the trailing edge of the cylindrical article in the inspection zone, the first and second predetermined phase angles differing approximately by 180 degrees.

6. The invention according to claim 1, wherein: the said first and second multiple polar sensor assemblies are rigidly mounted coaxially within a housing by means of a non-metallic potting compound.

7. The invention according to claim 1, wherein:

second excitation windings of the first and second multiple polar sensor assemblies are connected in subtractive magnetic polarity relative to each other to prevent inducing circulating currents into the cylindrical article stream.

8. The invention according to claim 1, wherein:

the angular positions of the polar sensors mounted in the first multiple polar sensor assembly are angularly offset relative to the angular positions of the polar sensors mounted in the second multiple polar sensor assembly by one half the angular degrees between the mounted polar sensors in each multiple polar sensor assembly, for overlapping sensing coverage of the cylindrical article.

9. The invention according to claim 8, wherein the first and second multiple polar sensor assemblies each have an equal number of mounted polar sensors.

10. The invention according to claim 2, wherein the magnetic shield is a non-ferrous metal cylinder having holes to conform around the extending portion of the mounted polar sensors.

11. Apparatus for detecting imperfections in the flange and shoulder portions of a cylindrical ferrous or non-ferrous metal container having a central longitudinal axis, comprising:

i) a multiple polar sensor assembly positioned in concentric relationship with the flange and shoulder portions of said container for generating a plurality of signals representative of the surface geometry of said container; said multiple polar sensor assembly comprising:

a) a hollow toroid core formed of ferromagnetic material, having an elliptical cross-section, with major and minor elliptical axes, the major elliptical axis of said core cross-section being disposed at a predetermined angle relative to the central axis of the hollow toroid core to form a conical shaped toroidal window, the longitudinal axis of the cylindrical container being disposed coaxially with the central axis of the hollow toroid core with the flange and shoulder portions within the conical shaped toroidal window;

b) a plurality of bores disposed in the inner circumference wall of the hollow toroid core, the axis of each bore being on the minor elliptical axis, and on a line intersecting the central axis of the hollow toroid core at a predetermined angle equal to an angle formed by a line drawn tangent to the flange and shoulder portions of the said cylindrical container;

c) a plurality of polar sensors mounted partially within the said plurality of bores so as to provide an extending portion outside the surface of the hollow toroid core, each mounted polar sensor coupling a symmetrical rotating magnetic field to the flange and shoulder portions of said container for detecting a rotating flux imbalance, said plurality of mounted polar sensors for generating a plurality of phase and amplitude modulated signals representative of the flaws in the shoulder and flange portions of the inspected container;

d) the said mounted polar sensors forming a conical shaped inspection zone equal to an angle formed by a line drawn tangent to the shoulder and flange portions of the inspected container relative to the longitudinal axis of the container for flux balance registry;

e) a first excitation winding wound within the hollow toroid core for inducing a first magnetic field throughout the hollow toroid core;

f) a second excitation winding wound around the outside of the hollow toroid core, being subdivided and wound between the extending portion of the mounted polar sensors for flux symmetry, said second excitation winding for inducing a second magnetic field throughout the hollow toroid core;

g) sine-cosine excitation being applied to the said first and second excitation windings for producing a rotating magnetic field throughout the hollow toroid core;

h) the hollow toroid core being separable for assembly reasons;

i) signal processing means for for processing said plurality of signals to extract flaw components.

12. The invention of claim 11, wherein each of the said polar sensors comprises:

a) a pick-up core formed of ferromagnetic material comprising:
i) a central cylindrical magnetic pole, a concentrically cylindrical outer magnetic pole provided around said central pole, and concentrically spaced to provide a pick-up coil space, and a base portion for connecting the two magnetic poles, the end opposite the base portion forming a planar sensing face portion, said planar sensing face being perpendicular to the axis of the central and cylindrical magnetic poles;
ii) Faraday shielding attached to the backside of the base portion, and having a grounded lead;
iii) a pick-up coil wound around the said central cylindrical magnetic pole, and having connecting means leading out through a hole in the base portion;
iv) a non-ferrous washer shaped magnetic shield disposed concentrically around the extending portion of the mounted polar sensor for shielding the hollow toroid core flux leakage.

13. The invention according to claim 11, wherein:

each of the said pick-up cores has a concave sensing face, for better flux coupling to the cylindrical geometry of the inspected container.

14. The invention according to claim 11, wherein the inspected container is rotated a predetermined angle for complete sensing coverage.

15. The invention according to claim 11, wherein the said signal processing means further comprises:

a) means to receive and amplify the said plurality of phase-amplitude modulated signals to a suitable level for extracting flaw components, each signal being further processed by:
i) a peak detector to determine amplitude data;
ii) a zero-crossing detector to determine phase angle data;

b) the plurality of detected signals being further processed in comparison circuitry to detect:
i) an individual signal having an anomalous amplitude deviation;
ii) an individual signal having an anomalous phase deviation; and generating a reject signal.

16. Apparatus for detecting imperfections in the flange portion of a cylindrical ferrous or non-ferrous metal container having a central longitudinal axis, comprising:

a) a hollow toroid core formed of ferromagnetic material;

b) a plurality of bores in one radial side wall of the hollow toroid core, the axes of said bores being parallel to the central axis of the hollow toroid core, and bores being centered in the radial portion of said core;

c) a plurality of polar sensors mounted partially within the said bores so as to provide an extending portion outside the surface of the hollow toroid core, each mounted polar sensor coupling a symmetrical rotating magnetic field to the flange of said container for detecting a flux imbalance, said plurality of polar sensors for generating a plurality of phase and amplitude modulated signals representative of the flaws in the flange portion of said container, the positions of said mounted polar sensors forming a circular geometry having flux coupling registry with the flange portion of the container during inspection;

d) a first excitation winding wound within the hollow toroid core, for inducing a first magnetic field throughout the hollow toroid core;

e) a second excitation winding wound around the outside of the hollow toroid core, being subdivided and wound between the extending portion of the mounted polar sensors for flux symmetry, said second excitation winding for inducing a second magnetic field throughout the hollow toroid core;

f) sine-cosine excitation being applied to the said first and second excitation windings for inducing a rotating magnetic field throughout the hollow toroid core;

g) the hollow toroid core being separable for assembly;

h) Faraday shielding surrounding a portion of the hollow toroid core, and being grounded;

i) signal processing means for processing said plurality of signals to extract flaw components.

17. The invention according to claim 16, wherein each of the said polar sensors comprise:

a) a pick-up core formed of ferromagnetic material; further comprising:
i) a central cylindrical magnetic pole disposed around said central pole, and concentrically spaced-to provide a pick-up coil space, and a base portion for connecting these magnetic poles, the end opposite the base portion forming a planar sensing face portion;

said planar sensing face being perpendicular to the axis of the central and cylindrical magnetic poles;
ii) Faraday shielding attached to the back side of the said base portion, and having a grounded lead;

iii) a pick-up coil wound around the central magnetic pole, and having connecting leads routed out through a hole in the base portion;

iii) a non-ferrous washer shaped magnetic shielding member concentrically surrounding the extending portion of the mounted polar sensor for shielding the hollow toroid core flux leakage;

iv) a hole in the base portion to provide connection access to the pick-up coil.

18. The invention according to claim 16, wherein the said signal processing means comprises:

a) means to receive and amplify said plurality of phase-amplitude modulated signals to a level suitable for extracting flaw components, each signal being further processed by:

i) a peak-detector to determine amplitude level;

ii) a zero-crossing detector to determine phase angle;

b) the plurality of detected signals being further processed in comparison circuitry to detect:

i) an individual signal having an anomalous amplitude deviation;

ii) an individual signal having an anomalous phase deviation.

* * * * *